United States Patent
Cho et al.

(10) Patent No.: US 11,951,479 B2
(45) Date of Patent: Apr. 9, 2024

(54) MICROFLUIDIC SYSTEM, METHOD FOR INHIBITING, DELAYING, OR REVERSING CELLULAR SENESCENCE USING MICROFLUIDIC SYSTEM, AND CELL OBTAINED THEREFROM

(71) Applicants: Konkuk University Industry-Academic Cooperation Foundation, Seoul (KR); Korea University Research and Business Foundation, Seoul (KR)

(72) Inventors: Ssang-Goo Cho, Seoul (KR); Aram Chung, Seoul (KR); Kyung Min Lim, Seoul (KR); Geunho Kang, Anyang-si (KR); Soobin Jang, Daegu (KR)

(73) Assignees: KONKUK UNIVERSITY INDUSTRY-ACADEMIC COOPERATION FOUNDATION, Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 133 days.

(21) Appl. No.: 17/389,138

(22) Filed: Jul. 29, 2021

(65) Prior Publication Data
US 2022/0032304 A1    Feb. 3, 2022

(30) Foreign Application Priority Data

Jul. 29, 2020 (KR) .................. 10-2020-0094616
Jul. 27, 2021 (KR) .................. 10-2021-0098400

(51) Int. Cl.
*B01L 3/00*    (2006.01)
*C12N 5/0775*  (2010.01)

(52) U.S. Cl.
CPC ...... *B01L 3/502746* (2013.01); *C12N 5/0665* (2013.01); *B01L 2400/0478* (2013.01)

(58) Field of Classification Search
CPC ...... B01L 2400/0478; B01L 3/502746; C12M 35/04; C12N 5/0665
See application file for complete search history.

(56) References Cited

U.S. PATENT DOCUMENTS

| | | | | |
|---|---|---|---|---|
| 2008/0131323 | A1* | 6/2008 | Kuczenski | G01N 15/147 422/68.1 |
| 2009/0148880 | A1* | 6/2009 | Fuhr | C12M 35/00 435/375 |
| 2015/0374887 | A1* | 12/2015 | Romero-Ortega | A61L 31/16 604/93.01 |

FOREIGN PATENT DOCUMENTS

| | | |
|---|---|---|
| CN | 201138312 Y | 10/2008 |
| CN | 110934879 | 3/2020 |

(Continued)

OTHER PUBLICATIONS

Menendez et al "mTOR-regulated senescence and autophagy during reprogramming of somatic cells to pluripotency: A roadmap from energy metabolism to stem cell renewal and aging", Cell Cycle, 10:21, 3658-3677, DOI: 10.4161/cc.10.21.18128 (Year: 2011).*

(Continued)

*Primary Examiner* — Jennifer Wecker
*Assistant Examiner* — Jonathan Bortoli
(74) *Attorney, Agent, or Firm* — CANTOR COLBURN LLP

(57) ABSTRACT

The present invention relates to a method of inhibiting, delaying, or reversing cellular senescence that includes having an isolated cell flow through a microchannel, and crashing the cell in flow into an impact surface installed on a flow path of the cell to apply a physical impact to the cell, resulting in inhibiting, delaying, or reversing senescence of (Continued)

the cell, while maintaining high biological activity, and in particular, it relates to a method that can further increase the value of a stem cell as a therapeutic cell for various degenerative diseases by maintaining undifferentiated state of the stem cell even during a long-term culture period to maintain multipotency, and to the cells obtained by the method.

10 Claims, 26 Drawing Sheets

Specification includes a Sequence Listing.

(56) References Cited

FOREIGN PATENT DOCUMENTS

| | | |
|---|---|---|
| EP | 3556845 | 10/2019 |
| KR | 1020120070219 | 6/2012 |
| KR | 1020200038172 | 4/2020 |
| WO | 2006007701 | 1/2006 |
| WO | 2020117856 | 6/2020 |

OTHER PUBLICATIONS

Ocampo et al "In Vivo Amelioration of Age-Associated Hallmarks by Partial Reprogramming" Cell, vol. 167, Issue 7, pp. 1719-1733. e12, (Year: 2016).*
Translation of (JP 2008-259490 A). (Year: 2008).*
Kuo et al ("Oscillatory Shear Stress Mediates Directional Reorganization of Actin Cytoskeleton and Alters Differentiation Propensity of Mesenchymal Stem Cells"). (Year: 2014).*
Shanko et al J.M.J. Microfluidic Magnetic Mixing at Low Reynolds Numbers and in Stagnant Fluids. Micromachines 2019, 10, 731. https://doi.org/10.3390/mi10110731 (Year: 2019).*
Goyal et al ("Isolation and Establishment of Mesenchymal Stem Cells from Wharton's Jelly of Human Umbilical Cord"). vol. 8, Iss 04 , Feb. 20, 2018 DOI:10.21769/BioProtoc.2735 (Year: 2018).*
Dudani et al "Pinched-flow hydrodynamic stretching of single-cells" Lab Chip, 2013, 13, 3728-3734 (Year: 2013).*
Alejandra Hernandez-Segura, et al., "Unmasking Transcriptional Heterogeneity in Senescent Cells", Current Biology (2017), vol. 27, pp. 2652-2660.
Chunsun Jiang, et al., "Serpine 1 induces alveolar type II cell senescence through activating p53-p21-Rb pathway in fibrotic lung disease", Aging Cell, (2017), vol. 16, pp. 1114-1124.
Deepraj Ghosh, et al., "Senescent mesenchymal stem cells remodel extracellular matrix driving breast cancer cells to a more-invasive phenotype", Journal of Cell Science, (2020), vol. 133, pp. 1-12.
Hou-Yu Chiang, et al., "MFG-E8 mediates arterial aging by promoting the proinflammatory phenotype of vascular smooth muscle cells", Journal of Biomedical Science, (2019), vol. 26, No. 61, pp. 1-14.
Jeremie Dalous, et al., "Reversal of Cell Polarity and Actin-Myosin Cytoskeleton Reorganization nder Mechanical and Chemical Stimulation", Biophysical Journal, vol. 94, Feb. 2008, pp. 1063-1074.
Joon-Il Jun, et al., "The Matricellular Protein CCN1/CYR61 Induces Fibroblast Senescence and Restricts Fibrosis in Cutaneous Wound Healing", Nat Cell Biol., (Jul. 2010); vol. 12, No. 7,pp. 676-685.
Mesut Erena, et al., "PAI-1-regulated extracellular proteolysis governs senescence and survival in Klotho mice", PNAS,(May 13, 2014), vol. 111, No. 19, pp. 7090-7095.
Naama Levi, et al., "The ECM path of senescence in aging: components and modifiers", The FEBS Journal, vol. 287, (2020), pp. 2636-2646.
Ossama Moujaber et al., "Cellular senescence is associated with reorganization of the microtubule cytoskeleton", Cellular and Molecular Life Sciences, (Jan. 1, 2019), pp. 1-15.
S. Gulberk Ozcebe, et al., "Effect of cellular and ECM aging on human iPSC-derived cardiomyocyte performance, maturity and senescence", Biomaterials, vol. 268, (2021), pp. 1-13.
Stefanie Kiderlen, et al., "Age related changes in cell stiffness of tendon stem/progenitor cells and a rejuvenating effect of ROCK-inhibition", Biochemical and Biophysical Research Communications, vol. 509 (2019), pp. 839-844.
Tomomi Ito, et al., "FGF-2 suppresses cellular senescence of human mesenchymal stem cells by down-regulation of TGF-b2", Biochemical and Biophysical Research Communications, vol. 359, (2007), pp. 108-114.
European Search Report—European Patent Application No. 21188286.5 dated Dec. 8, 2021, citing references listed within.
Gulfam Muhammad, et al., "Stem cell research trends using microtechnology" (translation), 2010, vol. 50, No. 11, (pp. 35-38).

* cited by examiner

[FIG. 1]
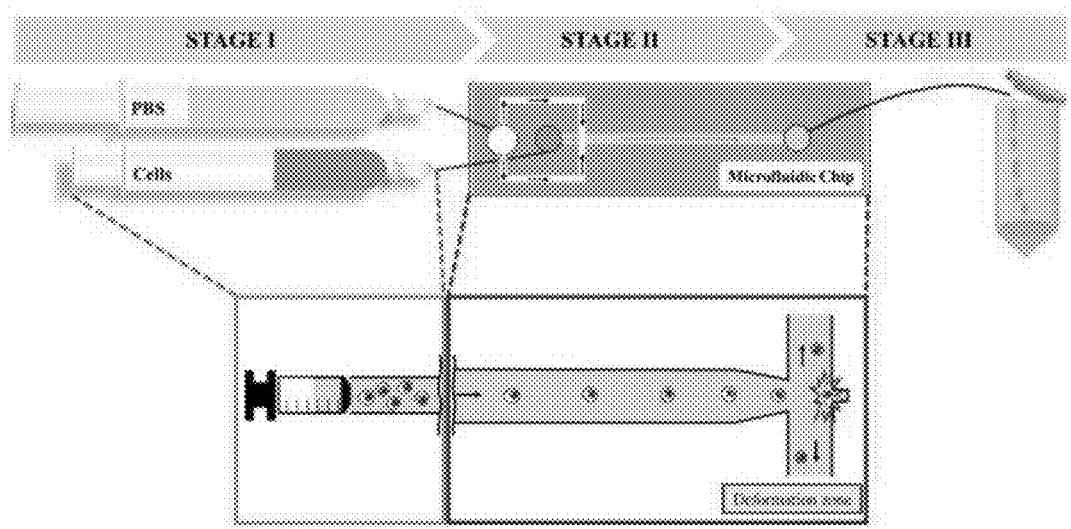
[FIG. 2]
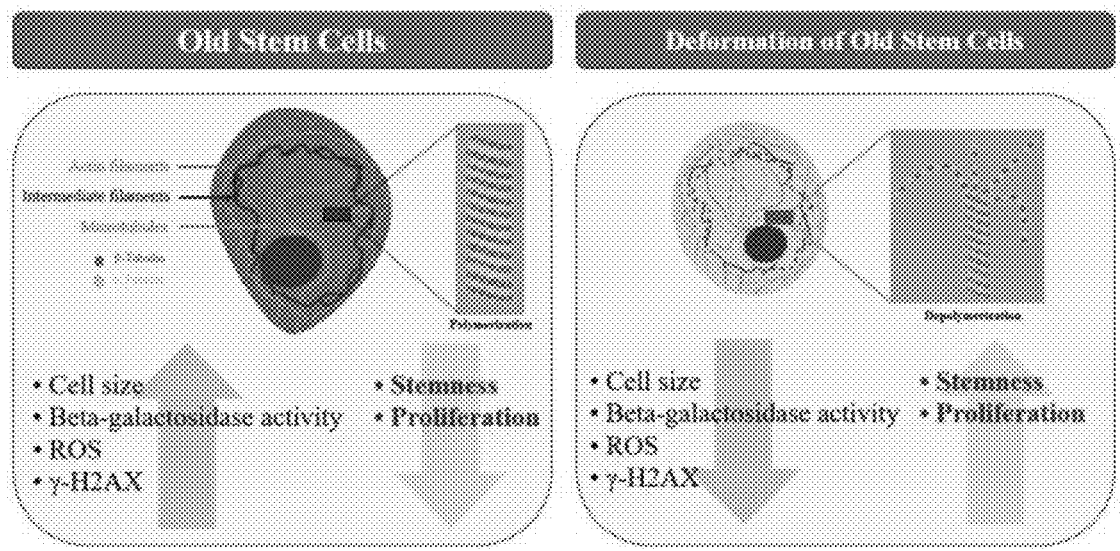

[FIG. 3]
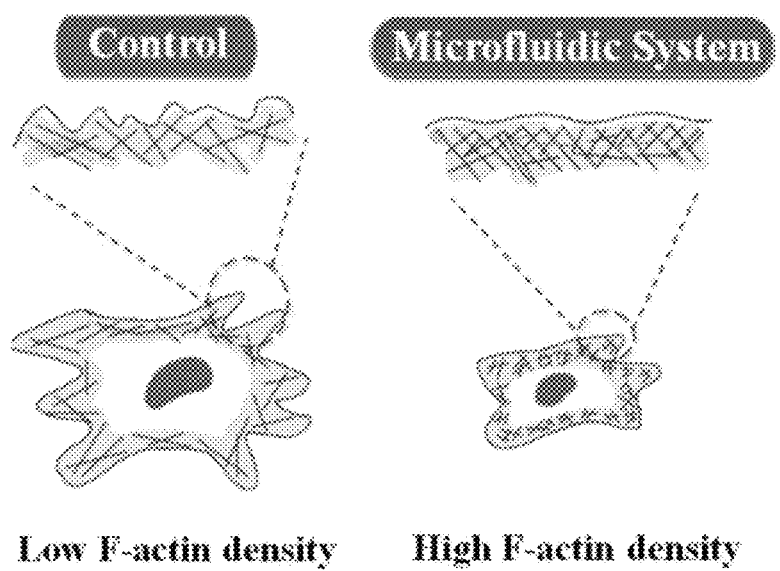

[FIG. 4]
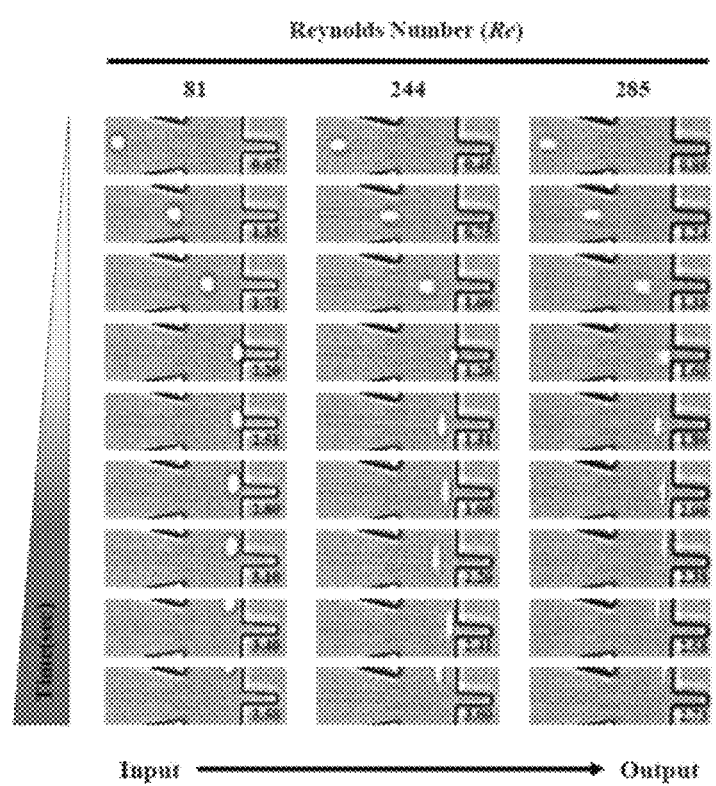

[FIG. 5]
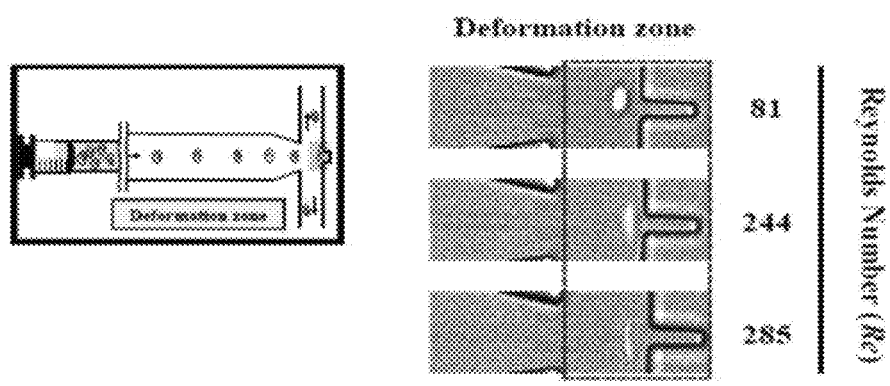
[FIG. 6]
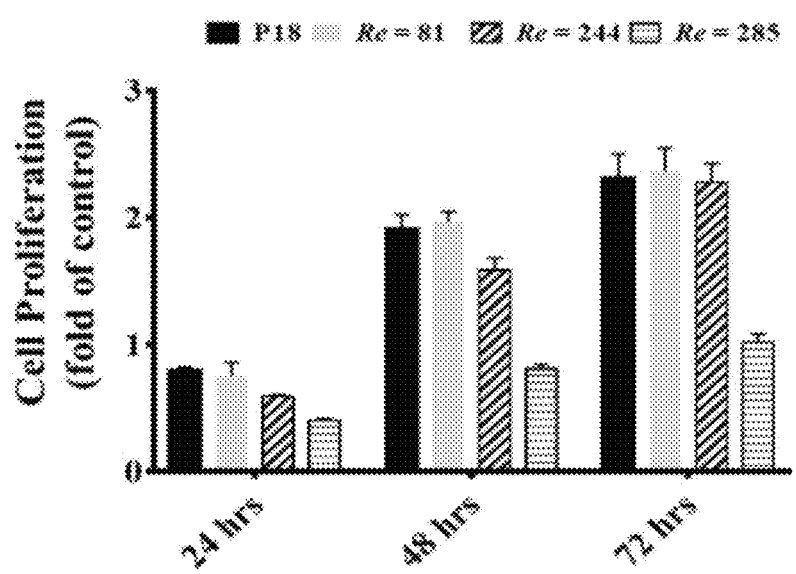

FIG. 8
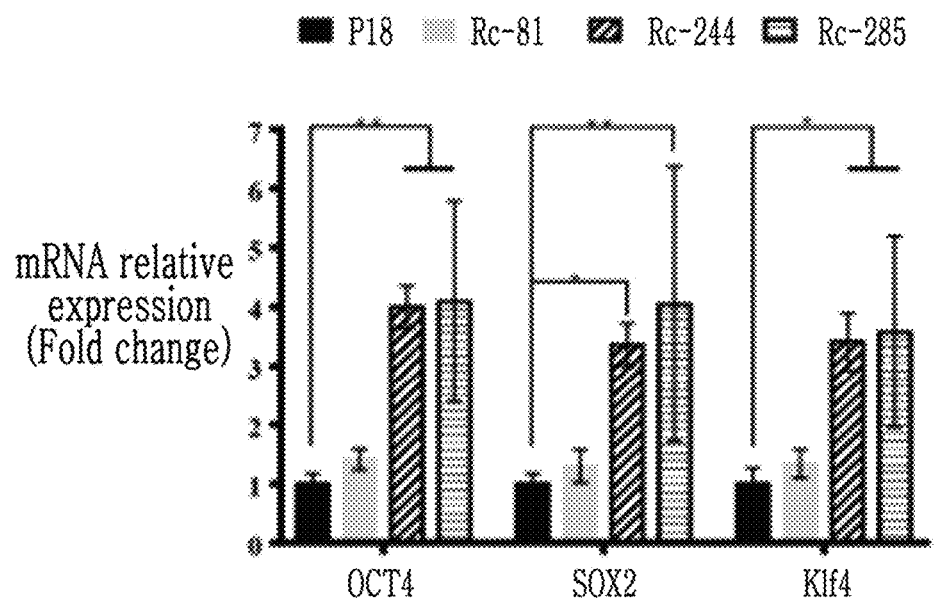
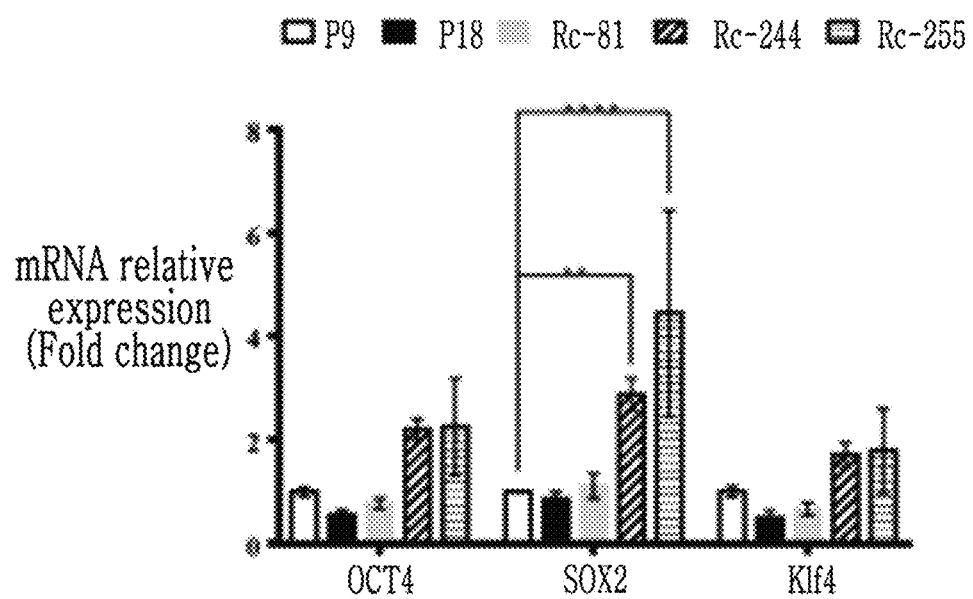

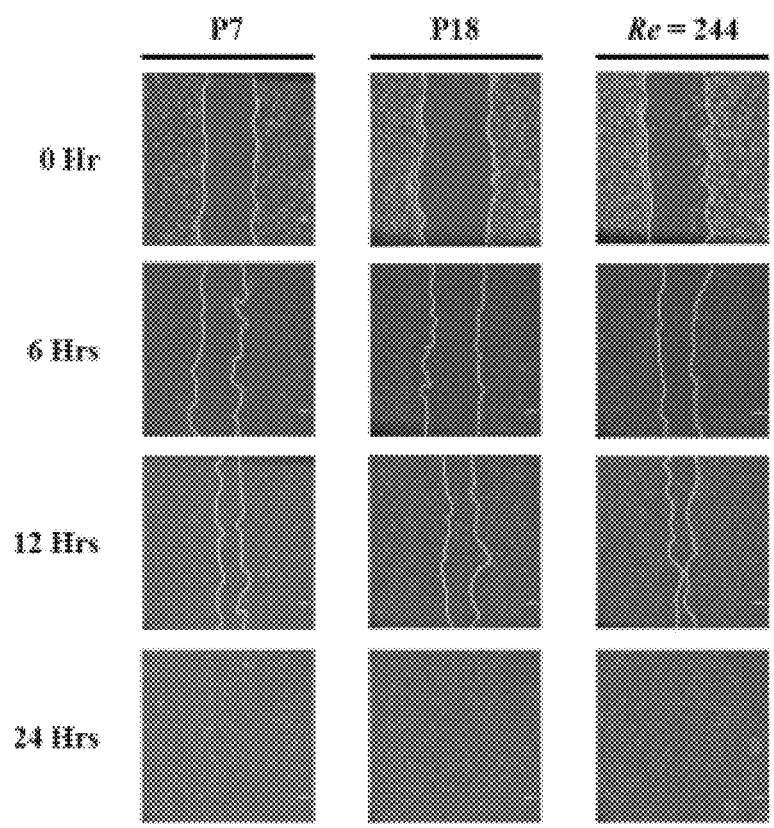
[FIG. 13]

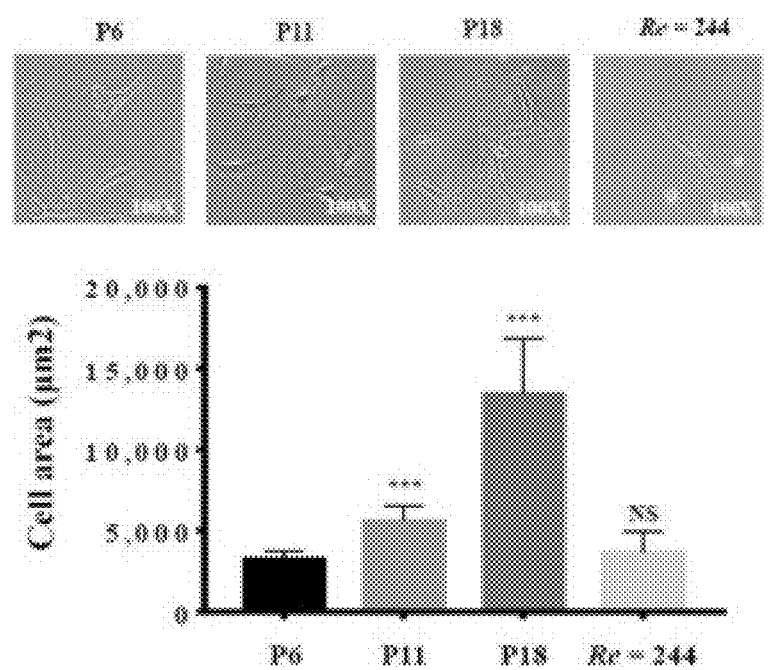
[FIG. 14]

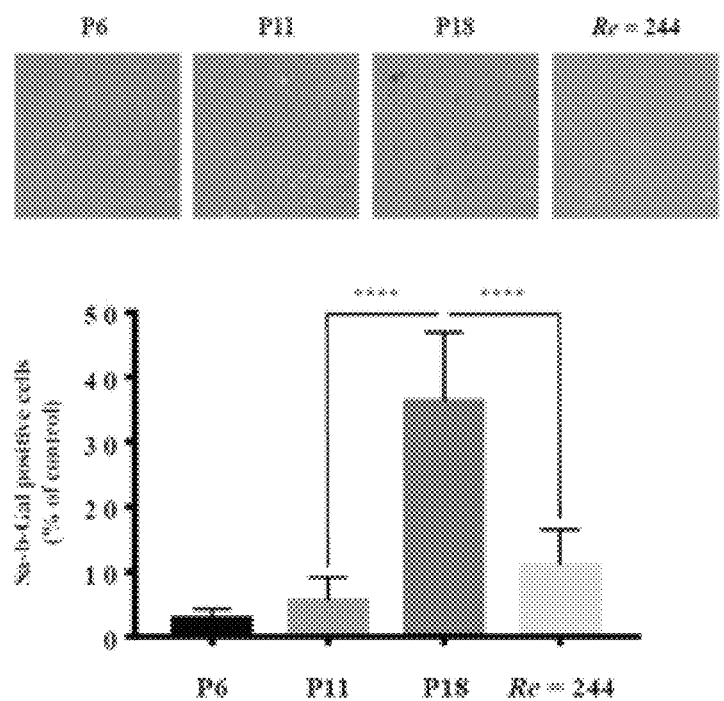
[FIG. 15]

[FIG. 16]
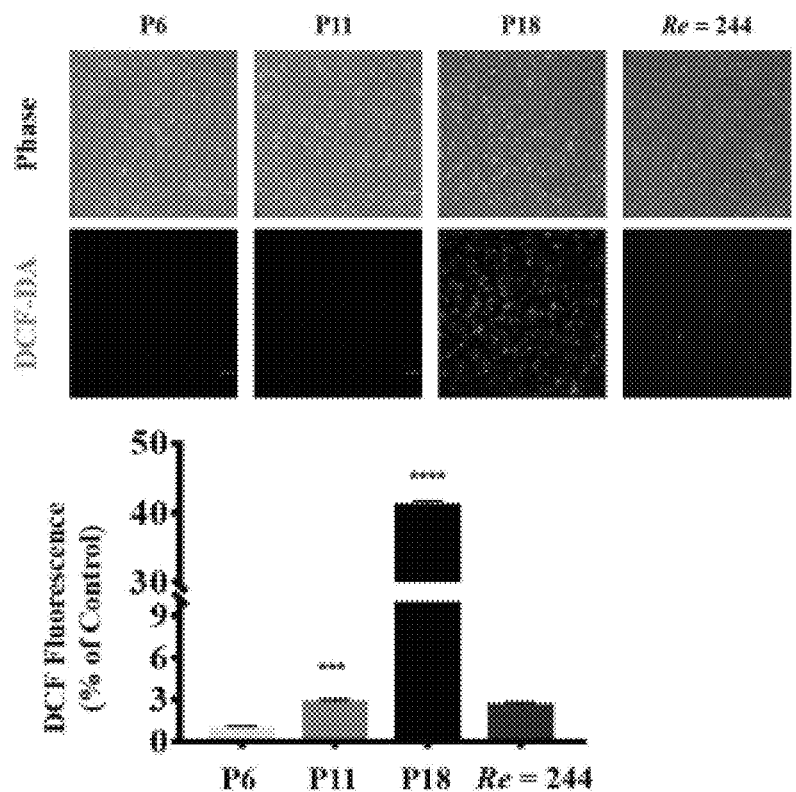
[FIG. 17]
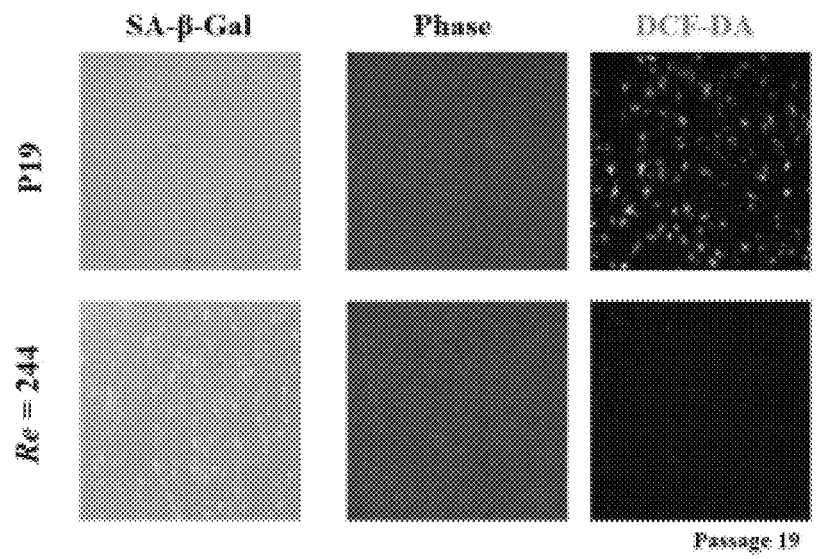

[FIG. 18]
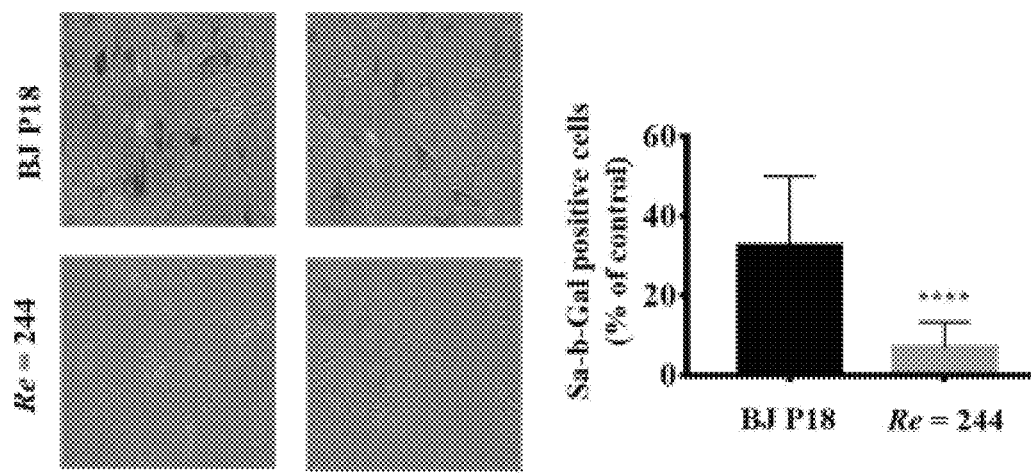

[FIG. 21]
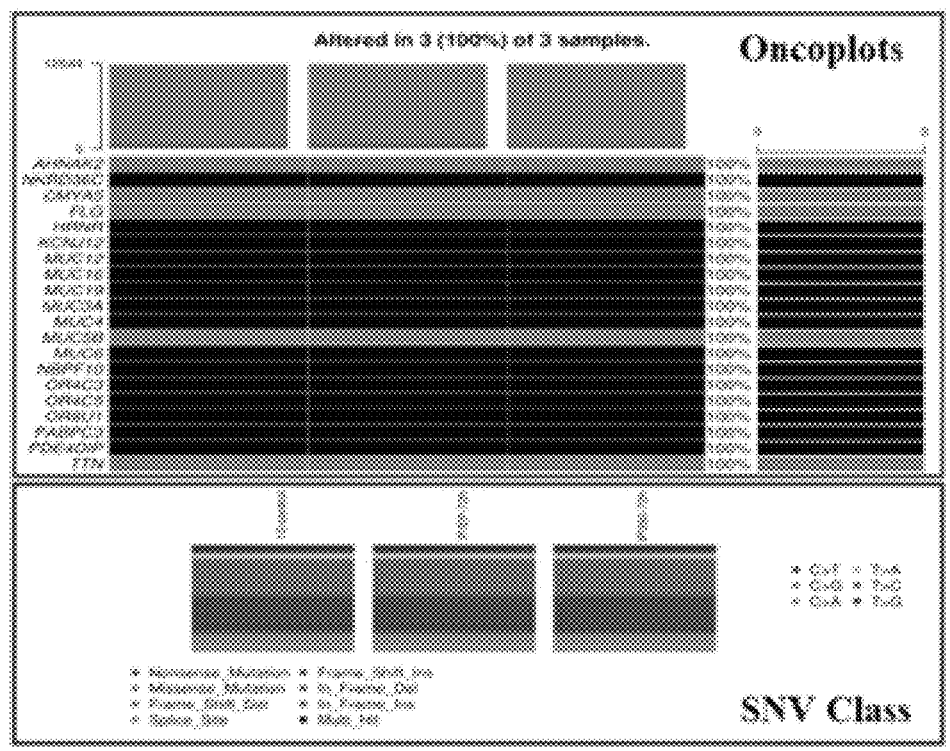

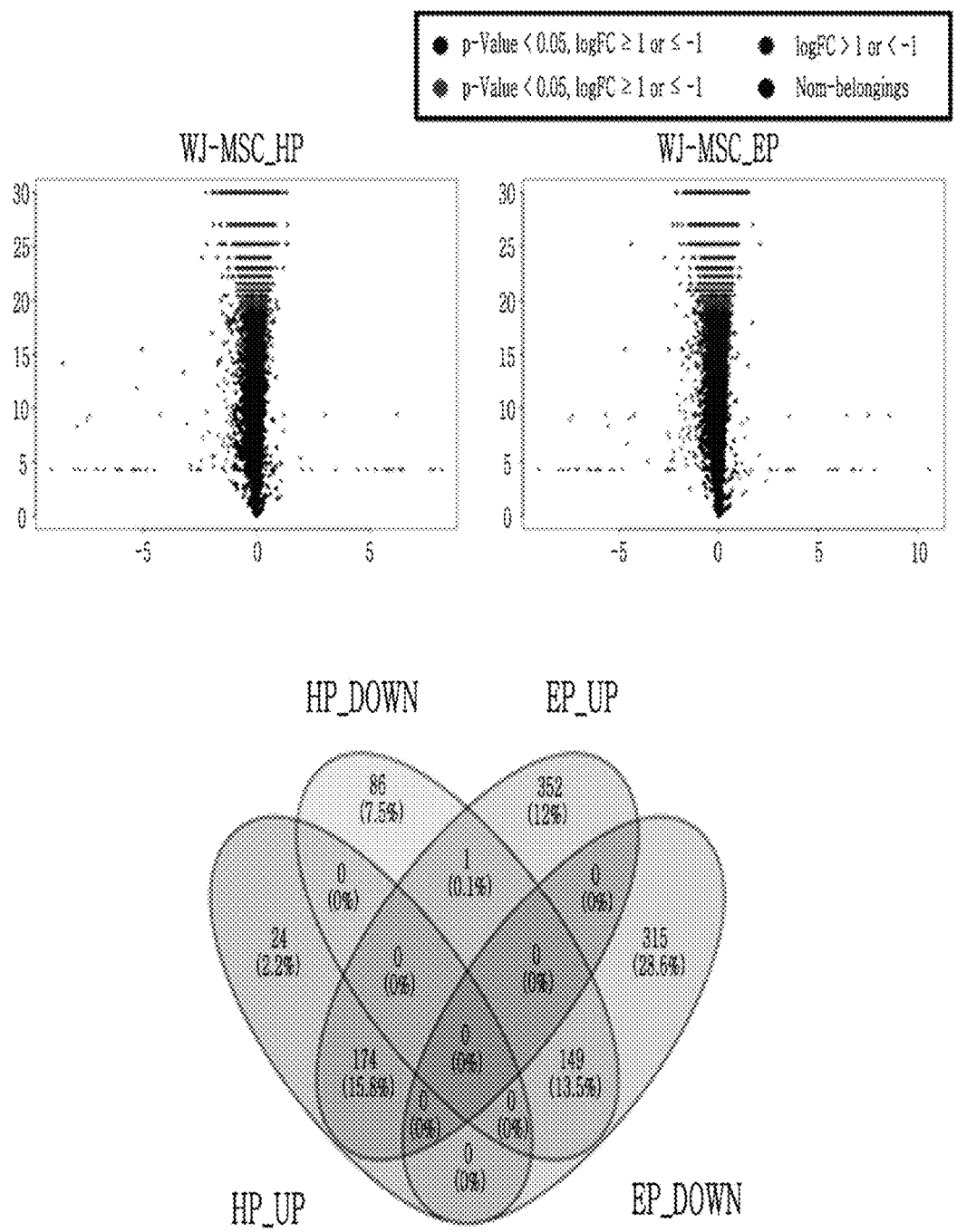

[FIG. 26]

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic_Oct4 F primer

<400> SEQUENCE: 1
cctgaagcag aagaggatca cc                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic_Oct4 R primer

<400> SEQUENCE: 2
aaagcggcag atggtcgttt gg                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic_Sox2 F primer

<400> SEQUENCE: 3
gctacagcat gatgcaggac ca                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic_Sox2 R primer
```

```
<400> SEQUENCE: 4
tctgcgagct ggtcatggag tt                                                    22

<210> SEQ ID NO 5
<211> LENGTH: 22
<212> TYPE: DNA
<213> ORGANISM: Artificial Sequence
<220> FEATURE:
<223> OTHER INFORMATION: Synthetic_Klf4 F primer

<400> SEQUENCE: 5
catctcaagg cacacctgcg aa                                                    22

<210> SEQ ID NO 6
<211> LENGTH: 22
<212> TYPE: DNA
<213> ORGANISM: Artificial Sequence
<220> FEATURE:
<223> OTHER INFORMATION: Synthetic_Klf4 R primer

<400> SEQUENCE: 6
tcggtcgcat ttttggcact gg                                                    22

<210> SEQ ID NO 7
<211> LENGTH: 22
<212> TYPE: DNA
<213> ORGANISM: Artificial Sequence
<220> FEATURE:
<223> OTHER INFORMATION: Synthetic_GAPDH F primer

<400> SEQUENCE: 7
gtctcctctg acttcaacag cg                                                    22

<210> SEQ ID NO 8
<211> LENGTH: 22
<212> TYPE: DNA
<213> ORGANISM: Artificial Sequence
<220> FEATURE:
<223> OTHER INFORMATION: Synthetic_GAPDH R primer

<400> SEQUENCE: 8
accaccctgt tgctgtagcc aa                                                    22
```

MICROFLUIDIC SYSTEM, METHOD FOR INHIBITING, DELAYING, OR REVERSING CELLULAR SENESCENCE USING MICROFLUIDIC SYSTEM, AND CELL OBTAINED THEREFROM

CROSS-REFERENCE TO RELATED APPLICATION

This application claims priority to and the benefit of Korean Patent Application Nos. 10-2020-0094616 and 10-2021-0098400, filed in the Korean Intellectual Property Office on Jul. 29, 2020, and Jul. 27, 2021, the entire contents of which are incorporated herein by reference.

BACKGROUND OF THE INVENTION

(a) Field of the Invention

The present invention relates to a method for inhibiting, delaying, or reversing cellular senescence by applying an impact to cells in flow using a microfluidic system, the microfluidic system, and a cell obtained from the method or the microfluidic system, in which senescence is inhibited, delayed, or reversed.

(b) Description of the Related Art

Cytoskeleton induces various intracellular changes through polymerization/depolymerization of actin in response to extracellular stimuli. These changes regulate cell migration and invasion, and affect the activity of ion channels present in the cell, ultimately leading to cell survival, proliferation, death, fluidity, and secretion through various intracellular signaling pathways.

Cellular senescence refers to an irreversible life phenomenon in which the cell cycle of cells exposed to various physical, chemical, and biological stresses is slowed and cell division is reduced or permanently stopped. With the progress of senescence, cell division not only decreases or stops, but also accumulates cell damage due to unstable transmission of genetic information. The causes of aging related to this genetic information include genome instability, loss of telomeres, and epigenetic changes.

However, senescence at the cellular level is a complex process that cannot be efficiently controlled by single-cause regulation. A method for effectively inhibiting or delaying cellular senescence or reversibly returning senescent cells to normal cells to have a phenotype similar to that of young cells has not yet been developed.

Meanwhile, mesenchymal stem cells (MSCs) first identified in bone marrow are totipotent cells with great potential in regenerative medicine. The mesenchymal stem cells may differentiate into several types of mesenchymal lineages, such as osteocytes, chondrocytes, adipocytes, myocytes, and fibroblasts. Since mesenchymal stem cells have immunomodulatory activity, it can be used as a composition for treating various autoimmune and inflammatory diseases, such as a transplant promoter, a fetal graft, and a host disease. In particular, the demand in regenerative medicine is continuously increasing due to the excellent therapeutic utility of mesenchymal stem cells. However, during in vitro expansion to secure a therapeutically effective amount of cells, the longer the culture period, the less the cells proliferate and the undifferentiated state cannot be maintained, and thus the regenerative ability and multipotency unique to stem cells is lost. Therefore, if a process for inhibiting senescence for stem cells or inducing reverse aging is developed, the therapeutic usefulness of stem cells can be significantly improved.

Numerous papers and patent documents are referenced throughout this specification and citations thereof are indicated. The disclosures of the cited papers and patent documents are incorporated herein by reference in their entirety to more clearly describe the level of the technical field to which the present invention pertains and the content of the present invention.

PRIOR ART LITERATURE

Patent Reference (Patent reference 0001) Korean application No. 2015-0167693

SUMMARY OF THE INVENTION

The present invention provides a method for inhibiting, delaying, or reversing cellular senescence and a cell in which senescence is inhibited, delayed, or reversed using the same.

The present invention also provides a method for maintaining or enhancing the multipotency of stem cells.

The present invention also provides a device for inhibiting, delaying, or reversing senescence of an isolated cell.

Other objects and advantages of the present invention will become more apparent from the following detailed description, claims, and drawings of the invention.

According to an embodiment of the present invention, the present invention provides a method for inhibiting, delaying, or reversing cellular senescence including:

having an isolated cell flow; and crashing the cell into an impact surface installed on a flow path of the cell to apply a physical impact to the cell.

The inventors of the present invention made intensive research efforts to develop a method for delaying senescence of various therapeutic and research cells, including stem cells, and maintaining high levels of biological activities such as survival rate, proliferation rate, and differentiation ability for a long period of time. As a result, the inventors found that in an in vitro environment including a flow channel and an impact surface, that is, in a microfluidic system, by allowing a target cell to flow with a certain parameter and crashing the cell into the impact surface to apply a physical impact to the cell, reorganization of the cytoskeleton may be induced, thereby significantly delaying, reversing, or inhibiting the cellular senescence. Specifically, the inventors have compared various aging factors, such as the cell size, the level of intracellular reactive oxygen species, and the expression levels of senescence-related proteins or genes of the cells that have passed through the microfluidic system as described above, with those of the control cells to which the microfluidic system as described above is not applied, to confirm the senescence inhibitory effect of the cells according to the present invention, and completed the present invention.

As used herein, the term "flow" comprises a fulid's flowing including a cell.

As used herein, the term "impact surface" refers to a surface into which a cell in flow crashes by being installed on the flow path while forming a predetermined angle with the flow path of the cell. The angle between the axis of the flow path and the impact surface may be about less than 180 degrees, for example, from about 10 degrees to about 170 degrees, from about 20 degrees to about 170 degrees, from about 20 degrees to about 160 degrees, from about degrees to about 160 degrees, from about 30 degrees to about 150 degrees, from about 40 degrees to about 150 degrees, from about 40 degrees to about 140 degrees, from about 50 degrees to about 140 degrees, from about 50 degrees to about 135 degrees, from about 50 degrees to about 130 degrees, from about 60 degrees to about 130 degrees, from about 60 degrees to about 120 degrees, from about 70 degrees to about 120 degrees, from about 70 degrees to about 110 degrees, from about 80 degrees to about 110 degrees, from about 80 degrees to about 100 degrees, from about 85 degrees to about 100 degrees, from about 85 degrees to about 95 degrees, or about 90 degrees, but not limited thereto. Any angle that enables collision with cells moving in the axial direction of the flow path by forming a predetermined angle without being in parallel with the axis of the flow path may be applied without limitation.

According to an embodiment, the flow path may be, for example, a T-shape in which cells flow in a straight line and then split at 90 degrees left and right from the flow direction at a certain point. In this case, the impact surface becomes the surface of the junction at perpendicular angles to the axis of the flow path. The impact surface may have a flat shape or may include a concave-convex structure including depression portions, protruding portions, or a combination thereof for efficient cell impact and cytoskeletal reorganization.

In an embodiment, the flowing may be performed by injecting a fluid containing cells into a microchannel in the microfluidic system according to an embodiment of the present invention to flow it.

As used herein, the term "microchannel" refers to a migration passage of a fluid having a hydraulic diameter of less than about 1 mm or a flow volume per minute of the fluid at the micro level (µl). For example, the flow volume of the fluid may be from about several tens to several thousands µl per minute, for example, from about several tens to several hundreds µl per minute, or from about several hundreds to several thousands µl per minute, and is not limited thereto.

The microfluidic system according to an embodiment of the present invention includes an inlet port for injecting cells or fluid, an outlet port for discharging cells, a microchannel connecting the inlet port and the outlet port to flow a fluid, and a control unit for controlling a flow rate of the microchannel.

According to an embodiment, the flowing may be performed according to predetermined parameters such that the reorganization of the cytoskeleton occurs without the physical impact causing cell death.

As used herein, the term "reorganization of the cytoskeleton" refers to a series of continuous processes in which tubulin proteins constituting microtubules that are cytoskeletal fibers are depolymerized by physical impact and then polymerized again, resulting in degeneration and recovery of the cytoskeleton. The present inventors found that during this cytoskeletal reorganization process, the density of actin, which is a constituent monomer of microfilament, another component of the cytoskeleton, increases, and the structure becomes dense, and resultantly it is confirmed that the characteristic phenotype of cells without senescence is reproduced.

The inventors found that when a physical impact of an appropriate energy is applied to a cell, for example, a senescent cell, to such an extent that degeneration and recovery of the cytoskeleton continuously occurs without completely destroying the cell, senescence-related phenotypes, such as, for example, the size of the cell, the level of reactive oxygen species, the expression levels of senescence-related proteins or genes, and actin density, have been changed to substantially inhibit, delay, or induce reverse aging.

Accordingly, the "predetermined parameters" refers to a series of hydrodynamic variables that can affect the amount of energy applied when the cell collides with the impact surface, such as, for example, a flow rate, density, or viscosity of the fluid containing the cells, and a diameter of a microchannel.

Specifically, the parameter may be determined by one or more factors selected from a density, a flow rate, a characteristic length, and a viscosity coefficient of a fluid containing the cells.

As used herein, the term "characteristic length" means a length that has the greatest influence on the flow, and may be, for example, the diameter of a microchannel.

More specifically, the parameter (Re) may be determined by Equation 1:

$$Re = \rho VD/\mu \quad \text{(Equation 1)}$$

In Equation 1, $\rho$ is the density of the fluid, V is the velocity of the fluid, D is the characteristic length of the fluid, and $\mu$ is the viscosity coefficient.

Equation 1 is an equation for deriving a Reynolds number. Reynolds number is a dimensionless number that quantitatively expresses a ratio of "inertial force" and "viscous force" in a fluid and may define flow conditions affected by various variables comprehensively.

According to an embodiment of the present invention, the flowing may be performed under the condition that the parameter (Re) having a value of less than 500. For example, the "Re" may be from about 1 to 500, from about 10 to 500, from about 10 to 450, from about 10 to 400, from about 10 to 350, from about 10 to 300, from about 10 to 290, from about 20 to 290, from about 30 to 290, from about 40 to 290, from about 50 to 290, from about 60 to 290, from about 70 to 290, from about 80 to 290, from about 90 to 290, from about 100 to 290, from about 100 to 280, from about 110 to 280, from about 120 to 280, from about 130 to 280, from about 130 to 270, from about 170 to 260, from about 180 to 260, from about 190 to 260, from about 200 to 260, from about 200 to 255, from about 205 to 255, from about 210 to 255, from about 210 to 250, from about 220 to 250, from about 225 to 250, from about 230 to 250, from about 235 to 250, from about 235 to 248, or from about 235 to 245, and is not limited thereto. In an example, the flowing may be performed with a non-viscos fluid, and in this case, the "Re" may be low to close 0 (zero).

According to an embodiment of the present invention, the distance from the point where a cell starts to flow in the microchannel to the impact surface may be from about 0.1 mm to about 50 mm. For example, the distance may be from about 0.1 mm to about 50 mm, from about 1 mm to about 50 mm, from about 0.1 mm to about 45 mm, from about 0.1 mm to about 40 mm, from about 1 mm to about 35 mm, from about 1 mm to about 30 mm, from about 1 mm to about 25 mm, from about 1 mm to about 20 mm, from about 2 mm to about 50 mm, from about 2 mm to about 40 mm, from about 2 mm to about 30 mm, from about 2 mm to about 30 mm, from about 3 mm to about 50 mm, from about 3 mm to about 40 mm, from about 3 mm to about 30 mm, from about 3 mm to about 25 mm, from about 3 mm to about 20 mm, from about 3 mm to about 15 mm, from about 5 mm to about 50 mm, from about 5 mm to about 40 mm, from about 5 mm to about 30 mm, from about 5 mm to about 20 mm, from about 5 mm to about 15 mm, from about 5 mm to about 10 mm, from about 3 mm to about 10 mm, from about 3 mm to about 8 mm, or from about 0.1 mm to about 50 mm, and is not limited thereto.

The method of the present invention may be applied without limitation to any cell that has a cytoskeleton. The cell may be, for example, a fibroblast, a stem cell including a mesenchymal stem cell, an embryonic stem cell, an induced pluripotent stem cell, or a combination thereof; an immune cell including a T cell, an NK cell, a B cell, a dendritic cell, a macrophage, or a combination thereof; a precursor cell of the fibroblast, the stem cell, or the immune cell; or a combination thereof, and may be any cell for research and therapeutics.

In an embodiment, the cell may be a stem cell or a precursor cell. As used herein, the term "precursor cell" refers to a unipotent cell that is only partially differentiated and shares a majority phenotype with stem cells.

As used herein, the term "stem cell" is an undifferentiated cell before differentiation into each cell constituting a tissue, and refers to cells having the ability to differentiate into a specific cell under a specific differentiation stimulus. The stem cells, unlike differentiated cells in which cell division is stopped, can produce the same cells as themselves by cell division (self-renewal), and when a differentiation stimulus is applied, the stem cells have the plasticity of differentiation that they can be differentiated into various cells depending on the nature of the stimulus. The stem cells used in the present invention have characteristics of stem cells, that is, undifferentiated, indefinite proliferation, and differentiation ability into specific cells, and any cell capable of inducing differentiation into a tissue to be regenerated may be used without limitation.

Specifically, the stem cells are mesenchymal stem cells.

As used herein, the term "mesenchymal stem cells" refers to stem cells having multipotency capable of differentiation into adipocytes, osteocytes, chondrocytes, muscle cells, nerve cells, or cardiomyocytes. The mesenchymal stem cells may be identified through their vortex shape and expression levels of the basic cell surface markers CD73(+), CD105(+), CD34(−), CD45(−) and also has a function of regulating the immune response along with multipotency.

For example, the mesenchymal stem cells may be umbilical cord-derived mesenchymal stem cells (WJ-MSC).

As used herein, the term "cellular senescence" refers to the expression of a natural aging phenomenon in which the function of a living organ deteriorates over time is expressed at the cellular level. For example, it means the stop or significant delay of growth and division due to various physical, chemical, and biological stresses (e.g., high oxygen conditions during successive passages and in vitro culture) that cells receive from the inside or outside. In undifferentiated cells such as stem cells, cellular senescence is a concept including a process in which stem cells lose their undifferentiated phenotype and lose their multipotent or pluripotent properties.

As used herein, the term "inhibition, delay, or reverse of cellular senescence" refers to including a series of processes of artificially temporarily inhibiting cellular senescence, delaying the rate of senescence, or reversibly recovering the biological function of cells lost due to aging to have a phenotype similar to non-senescent young cells. Accordingly, the term "inhibition of cellular senescence" may also be expressed as "delaying cellular senescence" or "inducing reverse aging of cells".

According to the present invention, when a constant energy impact is applied to the cells flowed according to the method of the present invention, the size of the cells decreases, the actin density of the cytoskeleton increases, the reactive oxygen species decreases, and the expression of senescence-related proteins or genes, including β-galactosidase and γ-H2AX is significantly inhibited, to effectively inhibit, delay, or reverse the cellular senescence progression.

According to another embodiment of the present invention, the present invention provides a cell in which senescence is inhibited by the method described above.

According to the present invention, the cells whose senescence is inhibited by the method of the present invention have high activity and proliferative capacity compared with the number of passages, and thus they can be usefully used as effective cell therapeutics or research cells even after long-term culture. In particular, stem cells may further increase their values as therapeutic cells for various degenerative diseases caused by irreversible tissue loss, by maintaining undifferentiated state and maintaining multipotency.

According to a specific embodiment of the present invention, the cell may be a cell in which the activity or expression of a protein selected from the β-galactosidase, γ-H2AX, and a combination thereof is inhibited.

As used herein, the term "inhibition of activity or expression" means that the activity or expression level of a specific protein or gene encoding the same is reduced. Therefore, inhibition of the activity or expression of a specific protein or gene means that the activity or expression of the protein or gene is reduced to such an extent that detection of the protein or gene is impossible or they are present at an insignificant level, and their biological functions are significantly reduced. For example, cells in which the activity or expression of the senescence-related protein or gene is inhibited by the method of the present invention has a decrease in activity or expression of the protein or gene by about 10% or more, a decrease of about 20% or more, a decrease of about 30% or more, a decrease of about 40% or more, a decrease of about 50% or more, or a decrease of about 60% or more, compared with a control cell to which the method of the present invention is not applied, but the range outside this is not excluded.

As described above, the cell of the present invention in which the activity or expression of the senescence-related protein or gene is significantly inhibited is a novel cell having a new protein expression profile that does not exist before.

According to another embodiment, the present invention provides a method for maintaining or enhancing the multipotency of a stem cell including:
hay an isolated stem cell flow; and
crashing the stem cell into an impact surface installed on a flow path of the stem cell to apply a physical impact to the stem cell.

Since the flowing, crashing, applying a physical impact, and a stem cell to which the physical impact is applied have already been described above, detailed descriptions thereof will be omitted to avoid excessive reiteration.

According to another embodiment, the present invention provides a device for inhibiting, delaying, or reversing senescence of an isolated cell, including:
an inlet port through which a fluid containing a cell is injected;
a microchannel through which the fluid injected through the inlet port flows;
an impact surface installed on a flow path of the microchannel; and an outlet port for discharging the cell that flowed along the microchannel and crashed into the impact surface.

According to an embodiment of the present invention, the device further includes a second inlet port through which an additional fluid containing or not containing a cell may be injected simultaneously or sequentially with the injection of the fluid containing the cell. In an embodiment, the additional fluid may be a cell-free buffer solution.

According to an embodiment, when the device includes both the first inlet port and the second inlet port, each of the first and the second inlet ports may have a separate connecting portion connected to the microchannel. The two connecting portions may be joined at one point before reaching the microchannel and connected to the microchannel through one flow path.

The features and advantages of the present invention are summarized as follows:
  (a) The present invention provides a method for delaying senescence of various cells and maintaining high biological activity compared with the number of passages using a microfluidic platform.
  (b) The present invention further increases the value of stem cells as therapeutic cells for various degenerative diseases by maintaining the undifferentiated state of the stem cells and maintaining their multipotency even during a long-term culture period.
  (c) The present invention may be used as a useful research tool for senescence mechanisms at the cellular level by not only delaying cellular senescence but also reversibly recovering the already advanced senescence and loss of biological functions of the cells.

BRIEF DESCRIPTION OF THE DRAWINGS

FIG. 1 is a schematic view showing the structure and operating method of a microfluidic device according to an embodiment of the present invention.

FIG. 2 is a schematic view showing the polymerization state (left) and depolymerization state (right) of tubulin protein, and the state of the cytoskeleton in the cells, in which the cytoskeleton is denatured by applying physical impact to a senescent stem cell according to the method of the present invention (right).

FIG. 3 is a schematic view showing F-actin proteins having a low density in the cell membrane of a senescent cell (control) with increased cell size (left), and having an increased density in a cell by reorganization of the cytoskeleton by applying a physical impact according to the method of the present invention (right).

FIG. 4 is a photograph showing cell morphologies for each flow condition over time observed through a high-speed microscope when the cells flow under different flow conditions (i.e., different Reynolds constantsRe of 81, 244, or 285) in the microfluidic device of the present invention.

FIG. 5 is photographs showing cell morphologies observed by a high-speed microscope at the vicinity of the impact surface in the microfluidic device when the umbilical cord-derived mesenchymal stem cells flow under different flow conditions (i.e., different Reynolds constant (Re) of 81, 244, or 285) in the microfluidic device according to an embodiment of the present invention.

FIG. 6 is a graph showing the proliferation rates of each cell after 24 hours, 48 hours, and 72 hours, respectively, after the umbilical cord-derived mesenchymal stem cells flowed under different flow conditions (i.e., Re of 81, 244, or 285) to crash into the impact surface in the microfluidic device, compared with the control group of 18 passages of umbilical cord-derived mesenchymal stem cells (P18) which is not treated by the microfluidic device.

FIG. 8 is graphs showing changes in expression of OCT4, SOX2, and Klf4 genes, which are undifferentiated markers, for each cell (Re=81, 244, or 285) compared with control cells (P9 and/or P18) after performing the same experiment as in FIG. 6.

FIG. 13 is photographs showing the migration of the cells of umbilical cord-derived mesenchymal stem cells of 7 passages (P7) and 18 passages (P18), and the umbilical cord-derived mesenchymal stem cells of 18 passages treated by the physical impact (Re=244) according to the method of the present invention (P18 HP) over time through a wound healing assay.

FIG. 14 is a microscopic photographs of the umbilical cord-derived mesenchymal stem cells of 6 passages, 11 passages, and 18 passages (P6, P11, and P18) and the umbilical cord-derived mesenchymal stem cell of 18 passages treated by the physical impact (Re=244) according to the method of the present invention through a microfluidic device, and a graph showing the cell area, i.e., cell size of the cells.

FIG. 15 is electron microscopic photographs of the cells of FIG. 14, which are SA-β-gal stained to confirm the expression of the senescence marker protein β-galactosidase in the cells, and a graph comparing the amounts of the stained cells measured from the photographs.

FIG. 16 is photographs and a graph showing the level of reactive oxygen species (ROS) in the cells of FIG. 15 through the amount of change in DCF-DA (dichlorofluorescin diacetate).

FIG. 17 is photographs showing measurement of β-galactosidase of senescent stem cells of 19 passages (P19), and the cells treated by the microfluidic device (Re=244) according to the present invention, through SA-β-Gal staining.

FIG. 18 is a graph and photographs showing the SA-6-gal stained cells in each of 18 passages of human neonatal foreskin-derived fibroblasts (BJ) (BJ P18) and the cells treated by the microfluidic device according to the present invention (Re=244).

FIG. 21 shows the results of comparison analysis by categorizing the genes in which mutations occur in common in the three groups of the cells of FIG. 20 into Oncoplots (genes with many mutations) and SNV (single nucleotide variants, genes in which one nucleotide is mutated) classes.

FIG. 22 is a Vann diagram showing the number of up-regulated genes which show significantly increased expression compared with those of control cell and down-regulated genes which show significantly decreased expression in the cells (HP) to which the microfluidic device of the present invention is applied and the cell (EP) which have been electroporated among the three groups of the cells of FIG. 20, by bioinformatics.

DETAILED DESCRIPTION OF THE EMBODIMENTS

Figure 7:
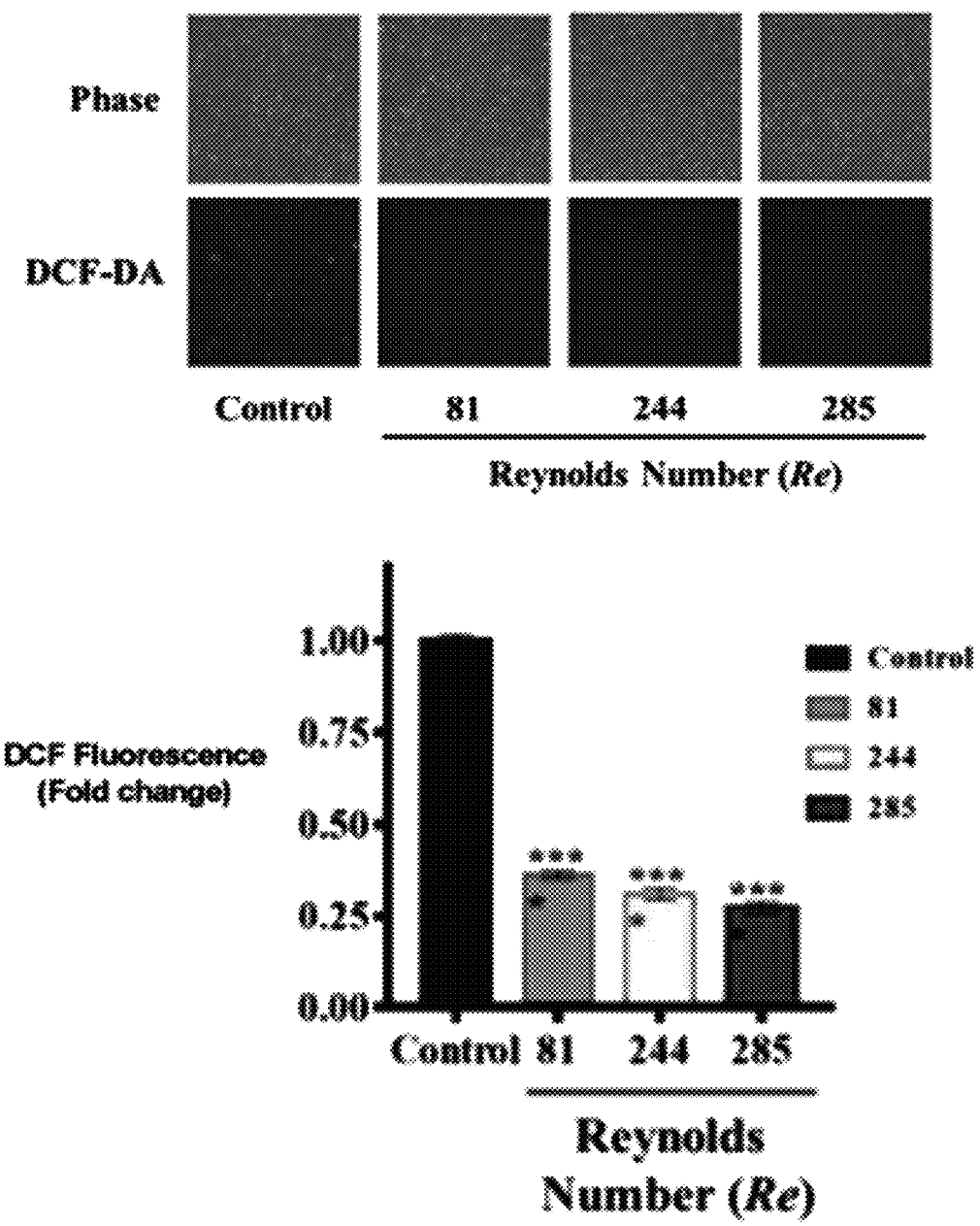
FIG. 7 is a graph and photographs showing the levels of intracellular reactive oxygen species (ROS), one of the senescence markers, using DCF-DA staining for each cell, compared with control cell (P18), after performing the same experiment as in FIG. 6.

Hereinafter, the present invention will be described in more detail through examples.

These examples are only for illustrating the present invention in more detail, and it will be apparent to those of ordinary skill in the art that the scope of the present invention is not limited by these examples according to the gist of the present invention.

EXAMPLES

[Experimental Methods]

1. Cultivation of Umbilical Cord-Derived Mesenchymal Stem Cells 1 ml of 0.1% trypsin/EDTA was added to umbilical cord-derived mesenchymal stem cells (WJ-MSC) of 18 passages cultured in a 100 mm culture dish (SPL, #20100) and then, incubated for 3 minutes in an incubator of 5% $CO_2$ and 37° C. Thereafter, 9 ml of α-MEM serum-free medium was added to a 15 ml tube (SPL) and then, centrifuged at 1,000 rpm for 3 minutes. After discarding a supernatant therefrom, a culture solution containing 1% P/S and 10% FBS was added to α-MEM in a 100 mm culture dish (SPL), and each $1\times10^6$ cells was seeded, and cultured for 48 hours before use in the experiment.

2. Cell-Microfluidics Experiments Using Microfluidic Devices 1 ml of 0.1% trypsin/EDTA was added to cells cultured in a 100 mm culture dish, and incubated for 3 minutes in an incubator of 5% CO 2 and 37° C. Then, a serum-free medium was added thereto and centrifuged at 1,000 rpm for 3 minutes to remove a supernatant. After adding 1 ml of FBS-added medium to the tube from which the supernatant was removed, 1 ml to 3 ml of the medium containing the cells was added to a 10 ml syringe (BD, #REF_302149), and the tube was connected to the inlet port of a syringe pump (Levodix, Fusion 100) Touch). After connecting the microfluidic device thereto, the experiment was performed, while changing the Reynolds constant under the condition of Re=75 to Re=290. Thereafter, after recovering the sample from the outlet port, centrifugation was performed under the same conditions as described above, and the number of cells was counted. Cell deformation was photographed using a microscope (Karl Zeiss, Observer A1) and a high-speed camera (Vision Research, Phantom V710L) at up to 580,000 frames per second. The photographed images were post-processed using ImageJ (NIH).

3. Quantitative Real-Time Reverse Transcription Polymerase Chain Reaction Analysis The cell culture medium was removed from the cells cultured in a 100 mm culture dish, washed 2 to 3 times with 1×PBS, 0.1% trypsin/EDTA 1 ml was added, and incubated for 3 minutes in an incubator of 5% CO 2 and 37° C. Then, a serum-free medium was added thereto and centrifuged at 1,000 rpm for 3 minutes to remove a supernatant. 300 μl of Trizol (Invitrogen) was added to the tube from which the supernatant has been removed, and RNA was extracted using direct-zol RNA Miniprep plus (Zymo, #R2070S) kit. The concentration of extracted total RNA was measured using a Nanodrop spectrophotometer (IMPEN, NanoPhotometer N60/N50), RNA was quantified, and then cDNA was synthesized using 2 μg of total RNA and M-MLV reverse transcriptase. qPCR was analyzed using 2×SYBR Green, and mRNA expression was calculated using GAPDH as a reference value.

Quantitative real-time reverse transcription polymerase chain reaction was performed using 2×SYBR green mix (EBT-1802), and the experimental results were normalized based on the expression level of GAPDH. The primers used are shown in Table 1. In addition, a total volume of 20 μl was analyzed by real-time PCR (7500, Amersham Pharmacia Biotech).

TABLE 1

| gene | Forward direction | Backward direction |
|---|---|---|
| Oct4 | CCT GAA GCA GAA GAG GAT CAC C | AAA GCG GCA GAT GGT CGT TTG G |
| Sox2 | GCT ACA GCA TGA TGC AGG ACC A | TCT GCG AGC TGG TCA TGG AGT T |
| Klf4 | CAT CTC AAG GCA CAC CTG CGA A | TCG GTC GCA TTT TTG GCA CTG G |
| GAPDH | GTC TCC TCT GAC TTC AAC AGC G | ACC ACC CTG TTG CTG TAG CCA A |

4. Beta Galactosidase (SA-β-Gal) Activity Assay

Senescent (17 passages to 26 passages) umbilical cord-derived mesenchymal stem cells and cells treated with a microfluidic device were prepared, and an SA-β-galactosidase analysis was performed according to a previously reported method (Nature protocols, 2009. 4(12): p. 1798). Briefly, cells were cultured in a 35 mm culture dish (SPL) until the proliferation state reached 80%, the culture medium was removed, 1 ml of 1×PBS (Veratech) was added, followed by washing twice at 100 rpm for 5 min, then, 1 ml each of 2% paraformaldehyde and 0.2% glutaraldehyde were added and then the resultant was fixed for 15 minutes. After discarding the fixative, 1 ml of 1×PBS was added and washed twice at 100 rpm for 5 minutes. After adding 1 ml of the prepared SA-β-gal staining solution, the resultant was incubated for 15 hours at 37° C. in the absence of $CO_2$. Thereafter, after discarding the SA-β-gal staining solution, 1 ml of 1×PBS was added, washed twice at 100 rpm for 5 minutes, 1 ml of 100% MeOH (Samjin Industries) was added, and then the resultant was left at room temperature for 30 minutes. Then, after discarding 100% MeOH, 1×PBS was added, and observed with an optical microscope (Fusion 100, Chemyx). The composition of the SA-β-gal staining solution was as follows: 200 mM citric acid/phosphoric acid, 100 mM K4[Fe(CN)6]3H$_2$O, 100 Mm K3[Fe(CN)$_6$], 5M Nacl, 1M MgCl$_2$, X-gal 50 mg/ml. SA-β-gal positive cells are shown in blue.

5. Reactive Oxygen Production Evaluation (H2DCF-DA)

In order to measure the accumulation amount of intracellular reactive oxygen species (ROS), 2',7'-dichlorodihydrofluorescein diacetate (H2DCFDA, Invitrogen) reagent was used. After culturing the umbilical cord-derived mesenchymal stem cells in α-MEM (1% P/S, 10% FBS) medium at 37° C., the culture medium was discarded, and the resultant was washed thoroughly with 1×PBS once or twice. Then, after adding the α-MEM (1% P/S, w/o FBS) culture solution, the solution was added so that the final concentration of H2DCFDA was 10 μM, and the cells were incubated at 37° C., under 5% $CO_2$ for 30 minutes. After discarding the culture medium to which 10 μM H2DCFDA was added, the resultant was washed once or twice with 1×PBS, and the umbilical cord-derived mesenchymal stem cells were directly observed using a fluorescence microscope (Nikon Eclipse TE2000-E).

6. Immunocytochemistry

Cells were fixed with 4% paraformaldehyde, washed 3 times with PBS, and 1×Triton X-100 was added thereto and then, incubated for 15 minutes. After washing 3 times with 1×PBS, the resultant was blocked with 10% bovine serum albumin at room temperature for 1 hour and 30 minutes before incubation with primary antibody. Then, incubated with the secondary antibody at room temperature for 40 minutes, and stained with DAPI. Then, the resultant was captured with a Zeiss LSM 800 confocal laser scanning microscope.

7. Cell Cycle Analysis Using Flow Cytometry

The cells were cultured in a 100 mm culture dish (SPL) until the proliferation state reaches 80%, the culture medium was removed therefrom, and 1 ml of 1×PBS (Veratech) was added thereto and then, as washed twice at 100 rpm for 5 minutes. After that, 1 ml of 0.1% trypsin/EDTA was added, and the resultant was incubated for 3 minutes in an incubator at 37° C. under 5% $CO_2$. After adding serum-free medium and centrifuging at 1,000 rpm for 3 minutes, the supernatant was removed. After discarding the fixative after the first centrifugation, 1 ml of 1×PBS was added, and the resultant was washed twice at 100 rpm for 5 minutes. Then, 1 ml of 70% EtOH was added, and the cells were fixed at room temperature for 30 minutes. Then, after centrifugation at 1,000 rpm for 3 minutes, EtOH was removed. Thereafter, 300 μl of PI/RNase staining buffer (5 mg/ml RNase, No. 51-6551AZ) was added, followed by reaction at room temperature for 30 minutes, and the cell cycle was analyzed using a flow cytometer (Beckman Coulter/CytoFLEX).

8. Analysis of Genetic Mutation

Cells of 9 passages among the umbilical cord-derived mesenchymal stem cells were cultured in a 100 mm culture dish (SPL) until the proliferation state reached 80% to 90%, and after removing the culture medium, 1 ml of 1×PBS (Veratech) was added and the resultant was washed twice or three times. Thereafter, 1 ml of 0.1% trypsin/EDTA was added and the resultant was incubated for 3 minutes in an incubator of 5% $CO_2$ and 37° C. Thereafter, serum-free medium was added, centrifugation was performed at 1,000 rpm for 3 minutes, and the supernatant was removed. Then, electroporation for the obtained cells of 10 passages were performed under the following conditions using the Neon™ Transfection System (MPK5000, Invitrogen™). That is, the cells were stimulated with a voltage of 1650 V and a pulse width of 10 ms. Then, the obtained umbilical cord-derived mesenchymal stem cells were seeded in a 100 mm culture dish with the number of $1×10^6$ cells, cultured in an incubator for 2 to 3 days, and the cells were separated and stored at −20° C. Thereafter, Exome sequencing was performed to selectively analyze only the Exon region within the gene by the NovaSeq 6000 analysis method (Macrogen) to analyze gene expressions of control cells that were the umbilical cord-derived mesenchymal stem cells of 10 passages were not treated, the cells that the electroporation method was applied, and the cells that passed through the microfluidic device according to the method of the present invention.

9. Structure and Operating Method of Microfluidic Devices

FIG. 1 is a schematic view showing a structure of a microfluidic device according to an embodiment, and a process of recovering the cells by applying an impact to the cells after flowing through them to cause deformation.

Referring to FIG. 1, the microfluidic device according to an embodiment includes one or more syringes (Syringe 10 ml LUER Lock, 302149, BD) for injecting target cells and a fluid such as a buffer solution and the like into the microfluidic device, one or more syringe pumps (Chemyx Fusion 100 Tuch) for pushing the one or more syringes at a constant speed for injecting the cells and/or the buffer solution in each syringe into the microfluidic device at the constant speed, a luer stub adaptor (LS25, luer stub, 25 ga (red)×0.5 in (12 mm)) for connecting the syringe and a power source providing power to the syringe pump, a tube (PEEK Tubing, 1/32" OD (outer diameter)×0.020" ID (inner diameter)) a camera (Optinityauto focus HD camera, KCS-50F)

for photographing movements and shape changes of the cells in the microfluidic device, and the like. The syringes may further be provided for separately injecting a target cell and buffer solution, or alternatively, one syringe may be used for simultaneously injecting a fluid containing the target cell into the microfluidic device. The other elements of the microfluidic device may further be provided or excluded, if necessary, and the diameter and length of the tube may appropriately adjusted according to an example.

The operation steps of the microfluidic device configured as described above may be divided into the following three steps:

First, the cells and a phosphate buffered aqueous solution (PBS) are respectively put into two syringes (each about 10 ml capacity), and then, each syringe is connected to a pump (Stage I in FIG. 1).

Second, the pumps connected to each syringe were operated by setting a flow into a Reynolds number (Re) of, for example, 1 to 500. Accordingly, the cells and PBS contained in the syringes may be injected into the microchannels in the microfluidic device and flow at a constant speed along the microchannels (Stage II of FIG. 1).

Third, the cells moving at a constant speed along the microchannels are crashed into an inner wall extending perpendicularly to the cell-moving direction, that is, an impact surface, and thus receive a physical impact of an appropriate force, and then, the cells deformed thereby are recovered through the outlet port (Stage III of FIG. 1).

10. In Vivo Analysis of Wound Healing of Wonded Mouse Model

In order to evaluate in vivo wound healing effect, 6 weeks old BALB/c nude female mice (CAnN.Cg-Foxn1nu/CrljOri SPFNAF Immunodeficient mice) were obtained from OrientBio Inc. Ltd. (Seongnam-si, Gyeonggi-do, Korea). The experiments were performed under recognition of the Institute of Animal's Control and Utilization Committee (IACUC) of Konkuk University (Recognition No.: KU20132). For being appropriately prepared for experiments, the mice were breeded for 1 week before the experiment in a room for which temperature and humidity were well controlled under a 12 hours' light and 12 hours' dark condition. The mice were divided to 6 groups as below:

(1) The control group, to which no treatment is applied;
(2) 1×PBS (buffer solution) treated group;
(3) The umbilical cord-derived mesenchymal stem cells of 6 passages (WJ-MSC P6) treated group;
(4) The umbilical cord-derived mesenchymal stem cells of 11 passages (WJ-MSC P11) treated group;
(5) The umbilical cord-derived mesenchymal stem cells of 18 passages (WJ-MSC P18) treated group; and
(6) The umbilical cord-derived mesenchymal stem cells of 18 passages treated by the physical impact through the microfluidic system according to an embodiment (WJ-MSC P18-HP) treated group. Each group has 4 mice. Before making wound, every mouse was anesthetized by intraperitoneal injection of Alfaxan (Careside Co., Ltd., Gyeonggi-do, Korea) in a dose of 60 mg/kg. Specifically, mice were anesthetized, and 2 wounds were made on a back of each mouse by using a sterilized biopsy puch (diameter 8 mm; Kai Industries, Tokyo, Japan). Then, 1×PBS (for the control group), or each of 100×L of PBS solutions including dispersed WJ-MSC P6, P11, P18, and WJ-MSC 18-HP cells in a concentration of $2 \times 10^6$ cells/ml were subcutaneously injected at four points around the wound of each mouse. For preventing contamination, the wounds were sealed by silicon (0.5 mm thickness), Tegaderm tape (1622W, 3M Coropated), and dressing (DUPOL). The size of the wound was determined by 30 cm scale, and recorded by using a digital camera. After 6 days of injection of the cells or PBS, the mice were scarified, and the skin tissues around the wound were incised. Then, the incised portions were fixed with 4% paraformaldehyde, dehydrated by alcohol, and paraffin embedding was performed. Then, the tissues were cut by 4 μm thickness in perpendicular to the surface of the wound, and the cutted tissues were placed on a slide pre-coated with 0.1% w/v poly-L-lysine (Sigma, St. Louis, MO). Subsequently, for visualization of the lesion and recovery of the tissues, each section was stained by hematoxyline and eosin, and resurfaced degree was evaluated. Further, the collagen synthesis rate was presumed by using Masson's trchrome staining method. In order to obtain tissue image, the slide was scanned by using a digital slide scanner (3D-Histech, H-1141 Budapest, Öv u. 3., Hungary).

[Experiment Result]

1. High-Speed Microscopy Observation Results

While cells were injected into the microfluidic device according to an embodiment of the present invention and then, flowed therein by applying a flow rate under various flow conditions, that is, a Reynolds constant Re of 75 to 290, a single cell flowing in the microfluidic device was observed with respect to changes near the impact surface of the microfluidic device, so-called, in a deformation zone by using a ultra-fast microscope camera (refer to FIGS. 4 and 5).

Referring to FIG. 4, when the flow rate was relatively low (Re=81), the cells moved to the outlet port immediately after colliding into the impact surface. However, as the flow rate was increased, for example, when Re was 244 or 285, the cells did not immediately move to the outlet port but stayed for a while due to a vortex formed around a stagnation point near the impact surface, which maximized deformation of the cells.

Referring to FIG. 5, as Re was increased, the deformation of the cells near the impact surface also increased. In other words, when Re=81, the cells maintained an oval shape, but when Re=244, the cells became flat, and when Re=285, the cells became flatter.

Appropriate Re required for the cell deformation turned out to vary depending on types of cells, but when Re was too high, the cells might be dissolved.

2. Viability of Umbilical Cord-derived Mesenchymal Stem Cells according to Flow Rate (Re) of Microfluidic Device After flowing cells in the microfluidic device according to an embodiment by applying flow rates corresponding to various Re's (75 to 290), proliferation rate changes of stem cells according to each Re were measured after 24 hours, 48 hours, and 72 hours, and the results are shown in FIG. 6.

As shown in FIG. 6, control P18 stem cells, that is, senescent stem cells of 18 passages exhibited a similar proliferation rate to that of the cells flowed at Re=81. In other words, at Re=81, almost no impact was applied to the cells, having almost no cell deformation effect. On the contrary, at Re=244, after 24 hours and 48 hours, the cell proliferation rate was decreased by about 20%, compared with the control group (P18) but after 72 hours, similar to that of P18 or at Re=81. In other words, at Re=244, the cell proliferation rate partially decreased due to the cell deformation in the beginning but was substantially equal to that of the control group (P18) having no treatment or at Re=81 showing almost no cell deformation effect over time, which could be interpreted as having an inhibitory effect on cellular senescence due to the cell deformation along with an adverse effect of the cell proliferation rate decrease due to the cell deformation. On the contrary, at Re=285, from the beginning (24 hours) to the 72 hours, the cell proliferation rate decreased by 50% or more, compared with all the other cells. In other words, when Re was too high, there might be a higher risk of cell lysis and the like than the anti-aging effect caused by the cell deformation.

From these results, it can be seen that the flow rate or Re in the microfluidic device affects the cell viability.

3. Analysis of Stemness and Senescence Marker Expression of Umbilical
Cord-Derived Mesenchymal Stem Cell After flowing aged umbilical cord-derived mesenchymal stem cells (WJ-MSC, P19) at a flow rate corresponding to various Re's through the microfluidic device, when a level of reactive oxygen species (ROS) in the cells, one of senescence markers, was checked in a DCF-DA staining method, as shown from FIG. 7, an amount of the reactive oxygens in the cells was significantly reduced under all the flow rate conditions, compared with that of the control group.

In addition, the amount of the reactive oxygen species (ROS) in the cells further decreased, as the flow rate increased, and particularly, at Re=285, ROS was reduced by 40% or so, compared with that of the control group.

Furthermore, expressions of OCT4, SOX2, and Klf4 genes, which worked as stemness indices of stem cells, were measured, and the results are shown in FIG. 8.

As shown from the left graph of FIG. 8, as the flow rate (Re) increased, the expressions of these genes increased, compared with that of the control group, and particularly, at Re=244 and 285, the expressions of the stemness marker genes 4 times or more increased, compared with that of the control group (P18). In addition, as shown from the right graph of FIG. 8, compared with those of umbilical cord-derived mesenchymal stem cells of intermediate passage (P9) as a control group, expressions of OCT4, SOX2, and Klf4 of the cells treated by the microfluidic device according to the present invention 2 times up to 4 times increased.

Figure 9:
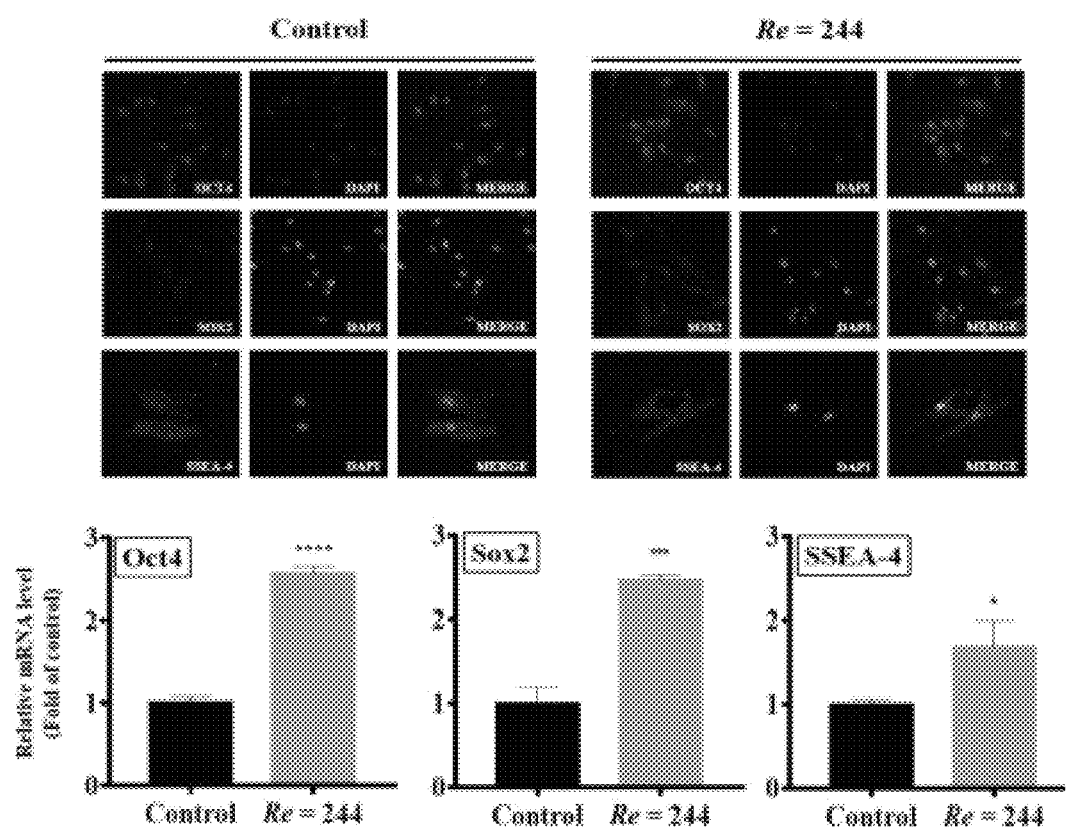
FIG. 9 is photographs and graphs showing the result compared with control cells (control) after performing the same experiment as in FIG. 6, and then measuring the mRNA levels of Oct4, Sox2, and SSEA-4, which are undifferentiated markers in a cell treated under the flow condition of Re is 244, by immunohistochemical staining.

In addition, the immunohistochemistry (INC) staining result of FIG. 9 also confirmed that expression levels of Oct4, Sox2, and SSEA-4 at Re of 244 significantly increased, compared with those of the control group. In addition, as shown from the graph of FIG. 9, particularly, a representative undifferentiated marker, Oct4, exhibited 2.5 times or more increase in an expression level of mRNA, compared with that of the control group.

The experiment results exhibited that when a physical impact was applied to the cells in the method of the present invention, the stem cells continued to be undifferentiated and thus maintained stemness. In other words, the cellular senescence was inhibited.

4. Cell Cycle Analysis of Umbilical Cord-Derived Mesenchymal Stem Cell

A cell cycle is divided into a cell division phase and an interphase for preparing the cell division. In addition, the interphase, which occupies about 90% of the cell cycle, is divided again into G1, S, and G2 phases. In general, cells live through a life of G1, S, G2, and M (mitosis) in order but in particular, have various interphase durations depending on the cells. In the present invention, in order to check whether or not the physical impact applied to the cells was involved in regulation of the cell cycle, the cells were flowed at a flow rate of Re=244 and analyzed with respect to cell cycles by using a fluorescence-activated cell sorting (FACS) method, and the results are shown in FIG. 10.

Figure 10:
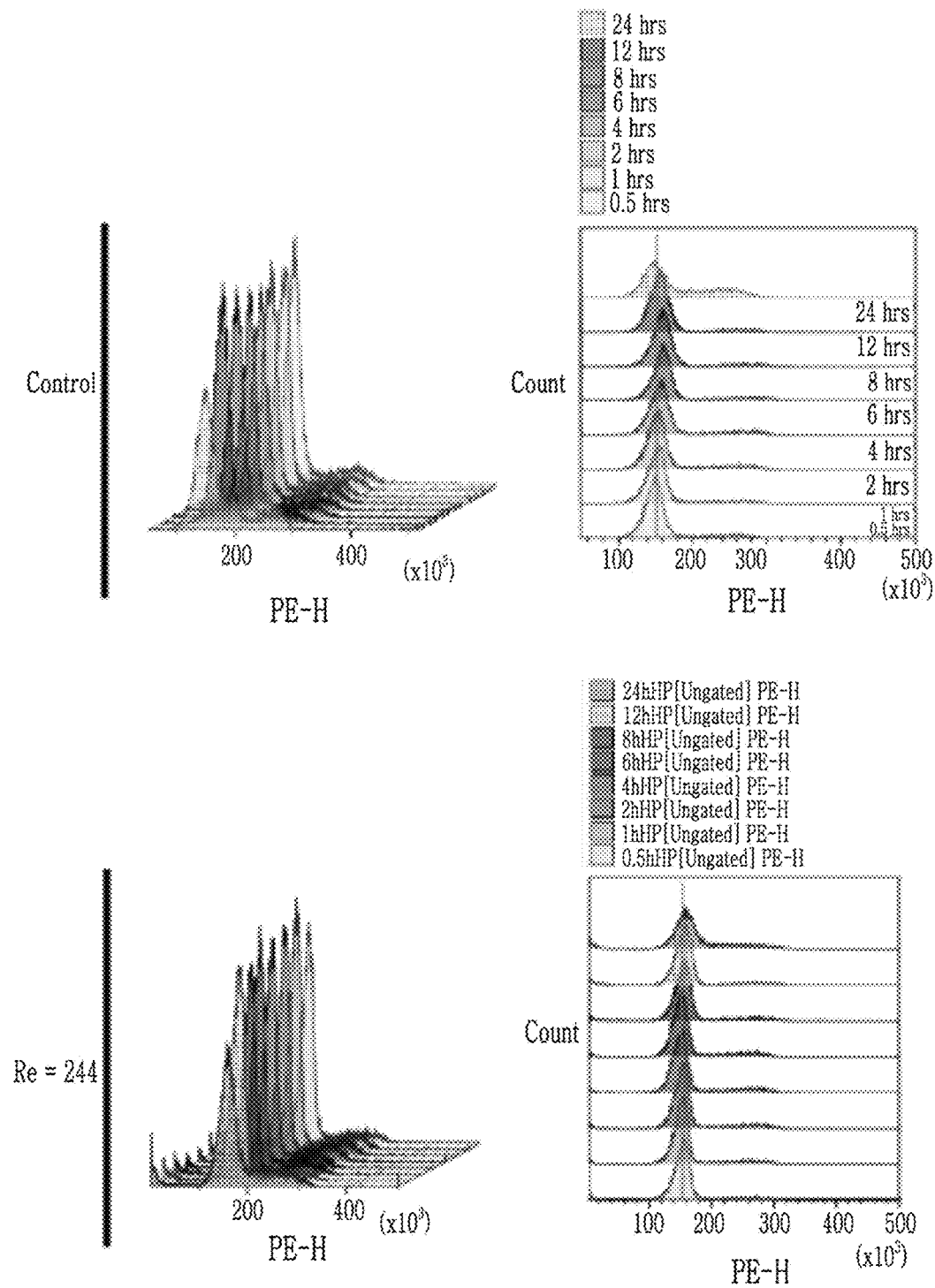
FIG. 10 is graphs showing the results of measuring cell cycle changes in the cells treated by the microfluidic device (Re=244) according to the present invention and the control cells.

As shown from FIG. 10, in the cell cycles of both the control group and the experiment group, since an arrest in the G2M phase or the S phase was not observed, the physical impact method through the microfluidic device according to the present invention did not change the cell cycles.

5. Expressions of Senescence Markers in Umbilical Cord-Derived Mesenchymal Stem Cells and Human Fibroblasts As metabolic changes occur due to cellular senescence, cells exhibit representative typical external features such as size and volume increases. Accordingly, after passing 18 passages of umbilical cord-derived mesenchymal stem cells through the microfluidic device of the present invention, with react to a size, the cells (Re=244) was compared with 6 passages (P6), 11 passages (P11), and 18 passages (P18) of the umbilical cord-derived mesenchymal stem cells not passing the microfluidic device.

As shown from the microscope photograph of FIG. 14, compared with the cells of the same passage (P18) not passing through the microfluidic device of the present invention, the cells passing through the microfluidic device (Re=244) exhibited a 4 times or more smaller size. In addition, referring to a bottom graph of FIG. 14 showing size comparison of the cells, the cells (Re=244) passing through the microfluidic device of the present invention had a size, which was smaller than that of the cells (P11) passing through an intermediate passage but a little larger than that of the young cells (P6), and accordingly, the aged cells of 18 passages was passed through the microfluidic device of the present invention and exhibited a significantly reduced size down to that of the young cells.

On the other hand, the cells were compared and experimented by using X-gal and DCF-DA staining methods in order to examine levels of β-galactosidase, one of cellular senescence markers, and intracellular ROS, and the results are shown in FIGS. 15 and 16.

Referring to FIG. 15, the number of positive cells for Sa-b-Gal among the cells (Re=244) passing through the microfluidic device of the present invention was reduced to ⅓ or less, compared with that of the control group (P18) but slightly higher than that of the younger cells of P6 or P11.

In addition, as for the DCF-DA expression, referring to FIG. 16, the cells (Re=244) passing through the microfluidic device of the present invention exhibited about 90% or more reduced content of ROS, compared with that of the control group (P18).

Additionally, β-galactosidase expressed by aged umbilical cord-derived mesenchymal stem cells of 19 passages (WJ-MSC, P19) and the cells (Re=244) passing through the microfluidic device of the present invention under the same experiment and confirmed by SA-β-Gal staining were similar results to those of FIGS. 15 and 16 (refer to FIG. 17).

In addition, referring to FIG. 18, after using human neonatal foreskin-derived fibroblasts (BJ P18) of 18 passages as a control group and applying an impact to the cells under the same condition (Re=244) as above, when β-galactosidase positive cells of two cell groups were measured, the number of Sa-b-Gal positive cells out of the cells applied with the impact (Re=244) also was reduced by nearly 20%.

Figure 19:
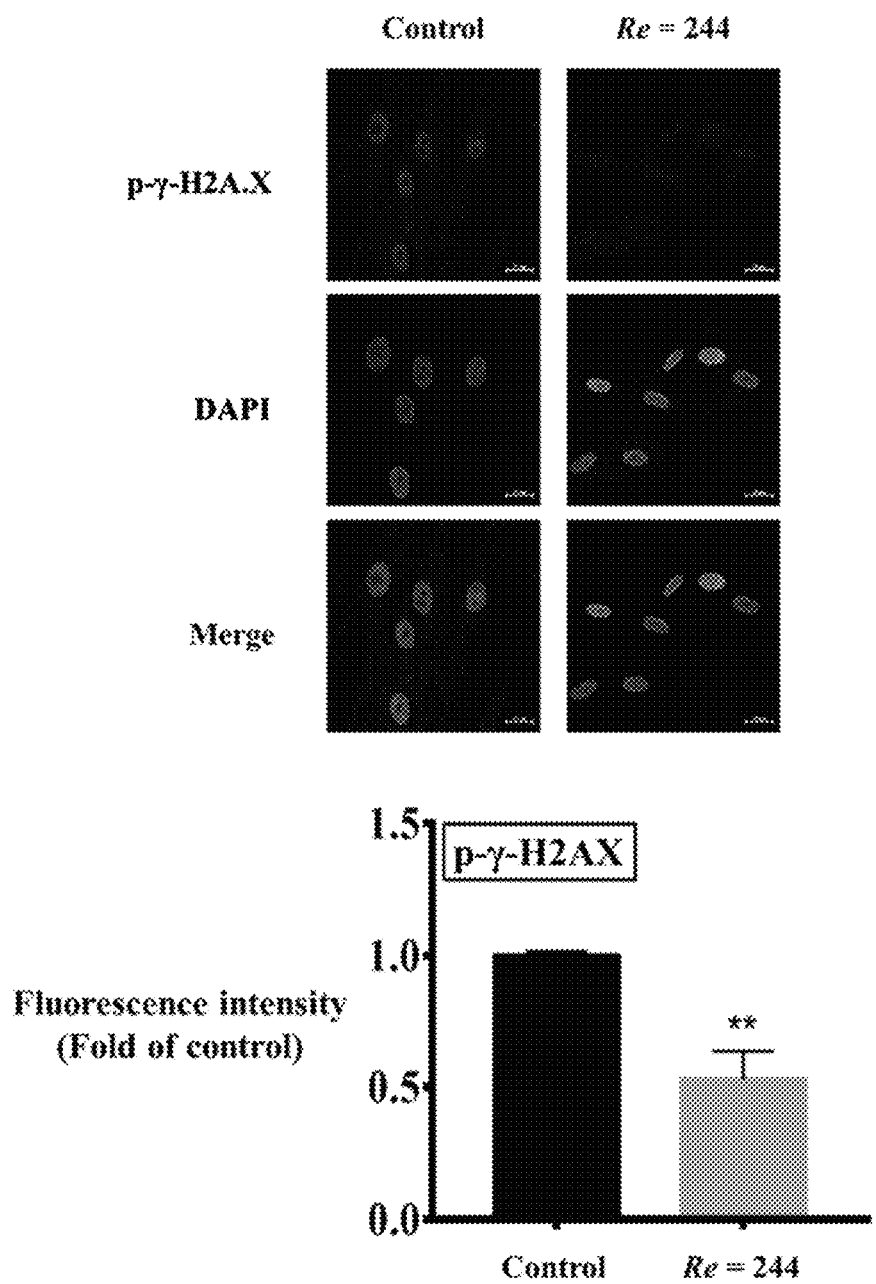
FIG. 19 is a graph and photographs showing the expression pattern of γ-H2AX, a senescence marker, in umbilical cord-derived mesenchymal stem cells pf 18 passages (P18) and cells (Re=244) obtained by passing the cells through a microfluidic device according to the method of the present invention, analyzed by histochemical staining, and a graph comparing their fluorescence intensity.

6. γ-H2AX Expression of Umbilical Cord-derived Mesenchymal Stem Cells Using Microfluidic Device When a double-strand break occurs in eukaryotic DNA, one of initial reactions occurring in a cell is phosphorylation of H2AX, one of the H2A molecules. In other words, γ-H2AX is one of the main markers for cellular senescence. Accordingly, the cells (Re=244) passed through the microfluidic device of the present invention were measured with respect to expression of γ-H2AX, as shown from FIG. 19, an expression rate thereof was reduced by 50% or more, compared with that of the control group (P18).

Figure 11:
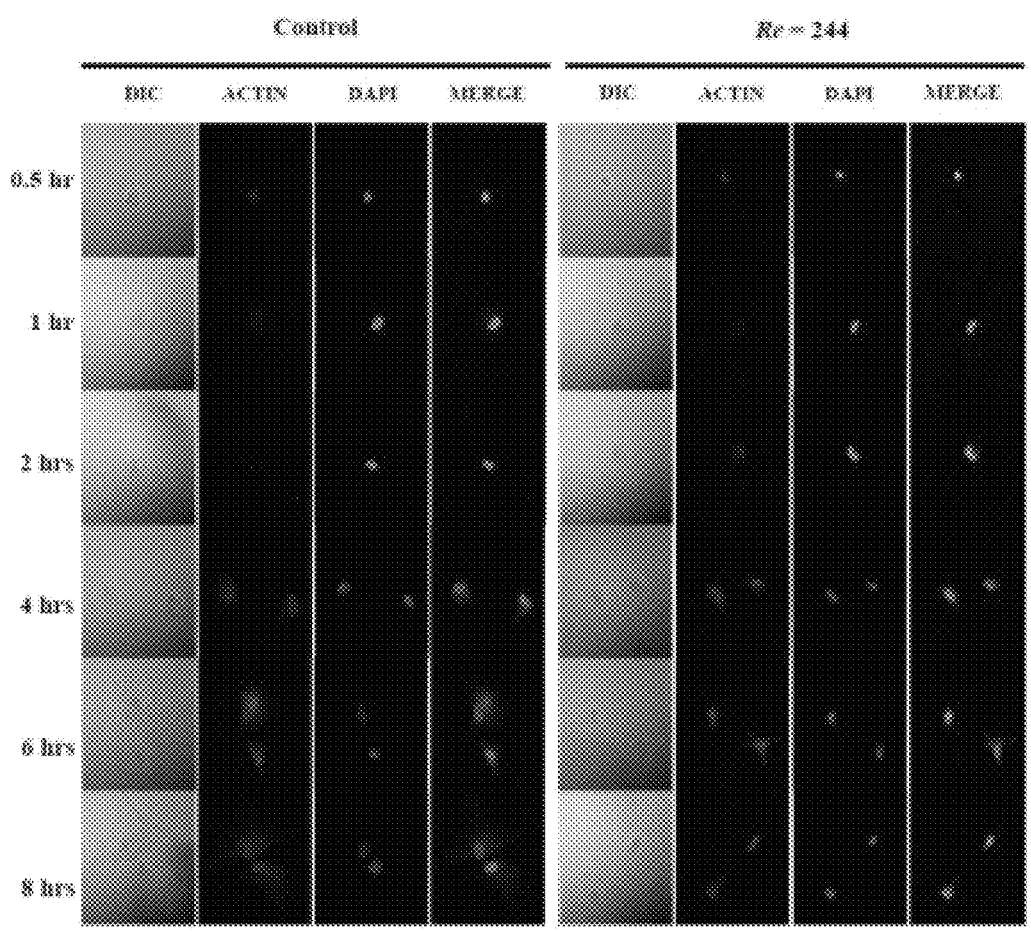
FIG. 11 is photographs of the cells of FIG. 10 analyzed by immunohistochemical staining of the expression pattern of actin protein, and also measuring the size of the cells over time.

7. Actin Expression in Umbilical Cord-Derived Mesenchymal Stem Cells Using Microfluidic Device The reorganization of cytoskeleton has been reported to regulate various activities such as cell survival, proliferation, death, cell motility, and protein selection (FEBS Letters 582 (2008) 2120-2127). In order to investigate whether or not the reorganization of cytoskeleton relates to reduction of a cellular senescence-related phenotype by the method of the present invention, umbilical cord-derived mesenchymal stem cells were flowed at Re=244 through the microfluidic device, and the recovered cells were compared with respect to expression of actin, one of cytoskeletons in an immunohistochemistry staining method. As a result, referring to FIG. 11, the cells (Re=244) passing through the microfluidic device of the present invention exhibited different actin expression patterns and cell sizes over times, compared with the cells of the control group not passing through the microfluidic device.

Figure 12:
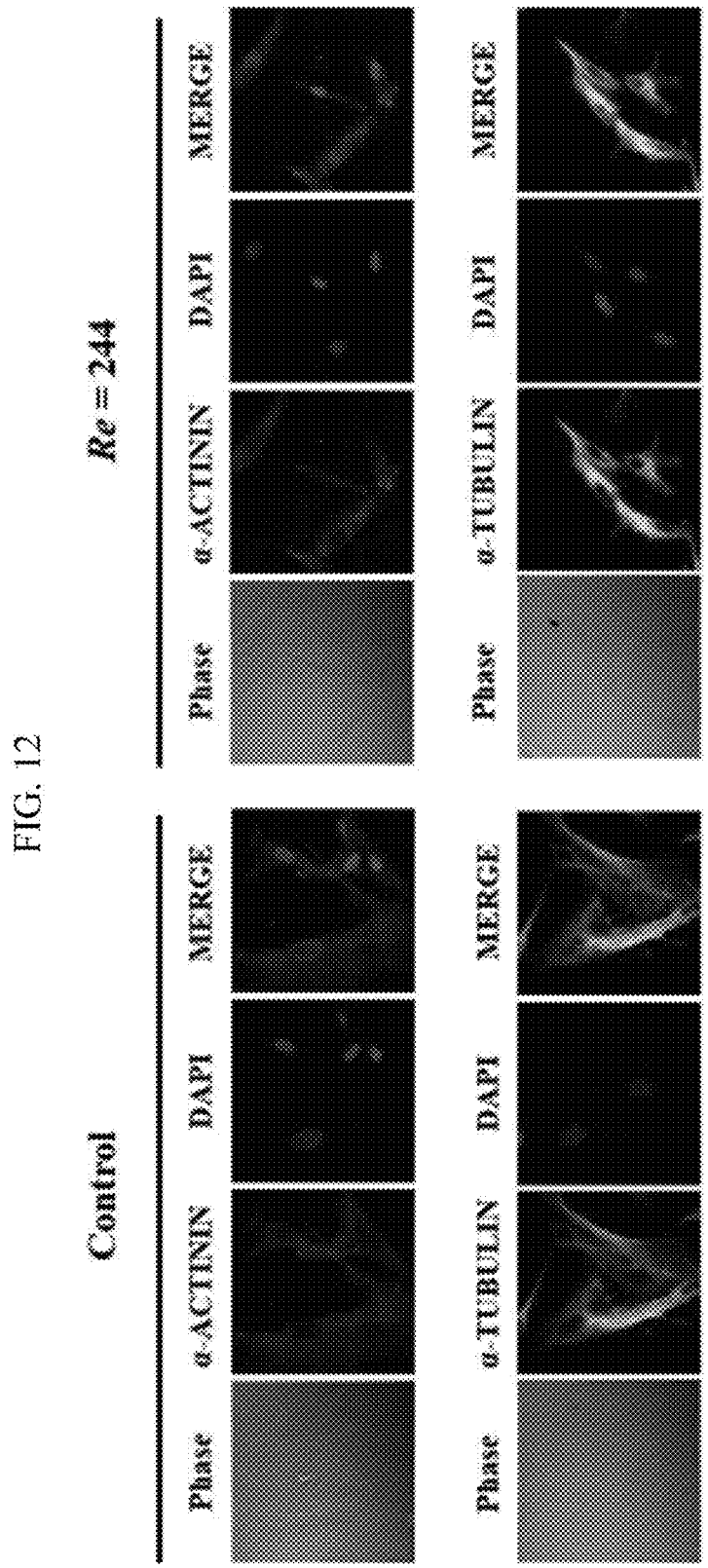
FIG. 12 is photographs obtained by analyzing the expression patterns of actinin and tubulin by immunohistochemical staining in the cells of FIG. 10.

In addition, FIG. 12 is a photograph analyzing the expression patterns of actinin and tubulin in the cells by immunohistochemical staining. The tubulin is also a protein constituting microtubules, which are cytoskeletal fibers involved in formation of cytoskeletons, and referring to FIG. 12, the cells (Re=244) passing through the microfluidic device of the present invention exhibited more clear expression of actinin and the tubulin, compared with those of the control group.

Without intending to be bound by a particular theory, the aforementioned results support that when a certain physical impact was applied to cells according to the method of the present invention, a temporary change occurred in cytoskeleton structures of the cells, and accordingly, the cellular senescence was inhibited, delayed, or reversibly reversed through the reorganization of the cytoskeleton inevitably followed thereby.

8. Analysis of Genetic Mutation

Figure 20:
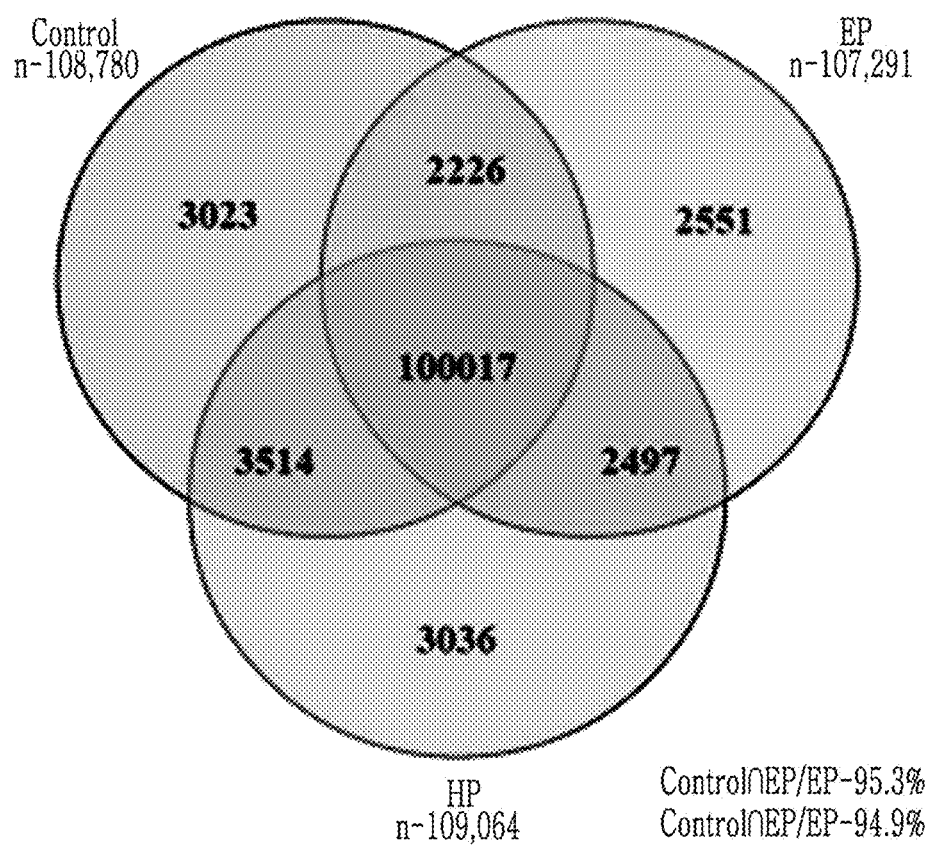
FIG. 20 is a result of analyzing the degree of mutation in genes between three groups of control cells (Control), cells to which the microfluidic device of the present invention is applied (HP), and electroporated cells (EP) through a Venn diagram.

FIG. 20 is a Venn diagram showing that when cells obtained by passing 10 passage cells of the umbilical cord-derived mesenchymal stem cells through the microfluidic device of the present invention or by applying electroporation to the 10 passage cells were analyzed with respect of genetic mutation and compared with cells of the control group having no treatment were analyzed, 94.9% of mutations between the control group and the microfluidic device-applied group of the present invention, 95.3% of mutations between the control group and the electroporation group were identical, and accordingly, 95% or more between the genetic mutations between all the groups were shared. In addition, as a result of comparatively analyzing whether or not there were common mutations among the tree groups, as shown in FIG. 21, mutations in the same gene in both of the groups were confirmed. This result confirms that the method of applying a physical impact according to the present invention for causing actin depolymerization of cells and thus reorganization of cytoskeleton brought no significant changes in gene expression.

9. Bioinformatics Analysis

A bioinformatics analysis was performed by using the microfluidic device according to the present invention to analyze differences in gene expression patterns in cells subjected respectively with electroporation and with a physical impact to 7 passage cells of umbilical cord-derived mesenchymal stem cells, and also in the control group cells having no treatment.

Specifically, RNA was respectively extracted from the three types of cells and then, used to analyze total mRNA in a NextSeq 500/550 method. Subsequently, in order to compare expression differences of the analyzed RNA, genes having a significant difference in expression levels were selected through a z-score and a p-value respectively from the control and the experiment groups, and the results are shown in FIGS. 22 and 23.

FIG. 22 is a view showing the number of each gene in a Venn diagram after analyzing up-regulated genes, which show significantly increased expression, and down-regulated genes, which show significantly decreased expression, in the electroporation cells (EP) and the cells (HP) to which the microfluidic device of the present invention was applied, by bioinformatics.

Referring to the Venn diagram of FIG. 22, the number of genes (HP-UP) showing increased expression in the cells (HP) subjected with a physical impact according to the present invention was 198 in total, and of which 174 genes (EP-UP) exhibited increased expression in the cells (EP) subjected with electroporation, and accordingly, these 174 genes exhibited increased expression in both cells. In addition, genes (HP-DOWN) exhibiting significantly decreased expression in the cells (HP) subjected with a physical impact according to the method of the present invention was 236 in total, of which 149 genes also were commonly expressed in the cells (EP) subjected with electroporation.

Figure 23A:
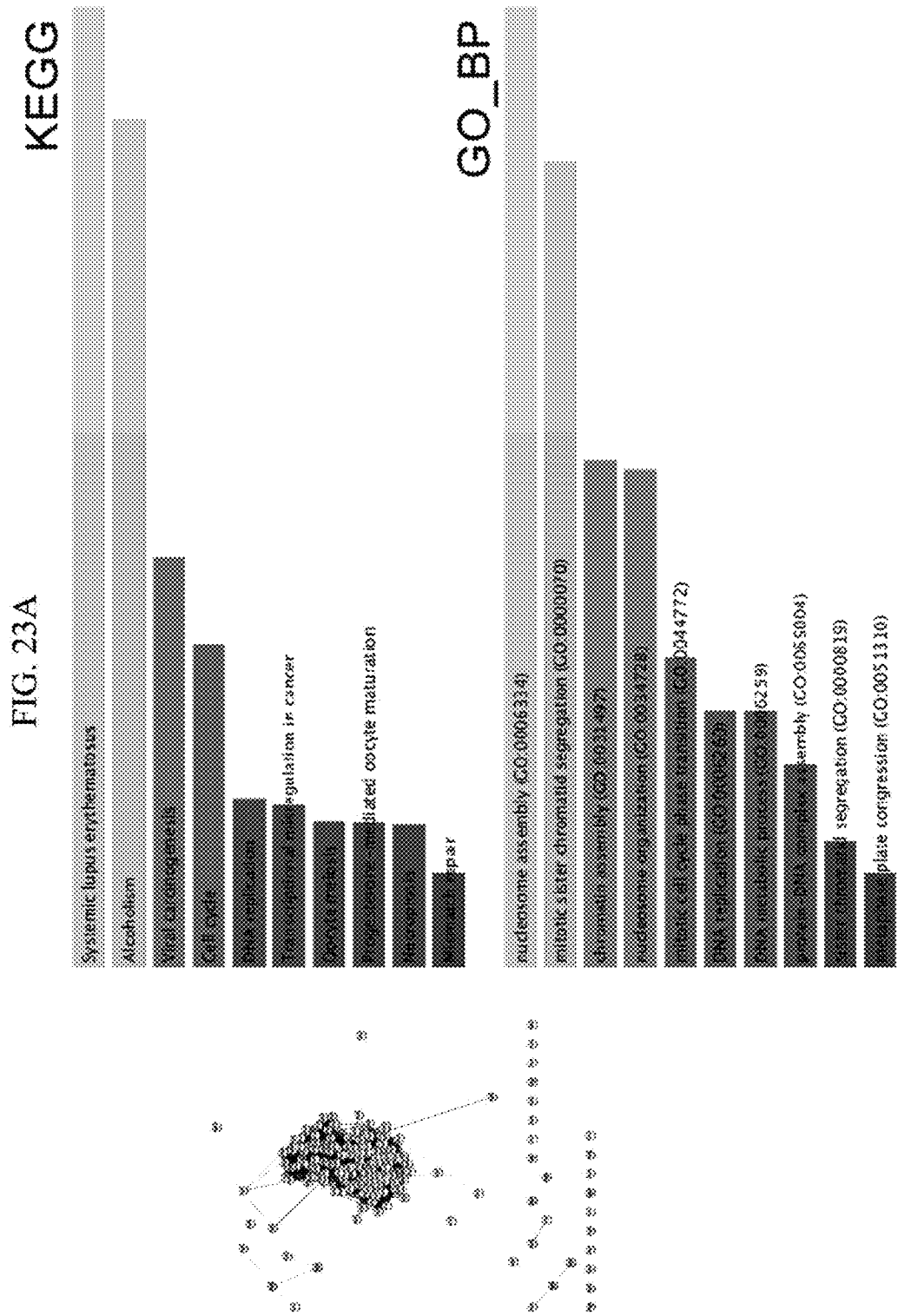
FIG. 23A is a view showing the patterns and types analyzed by gene ontology (GO), etc. of an up-regulated genes with increased expression.
Figure 23B:
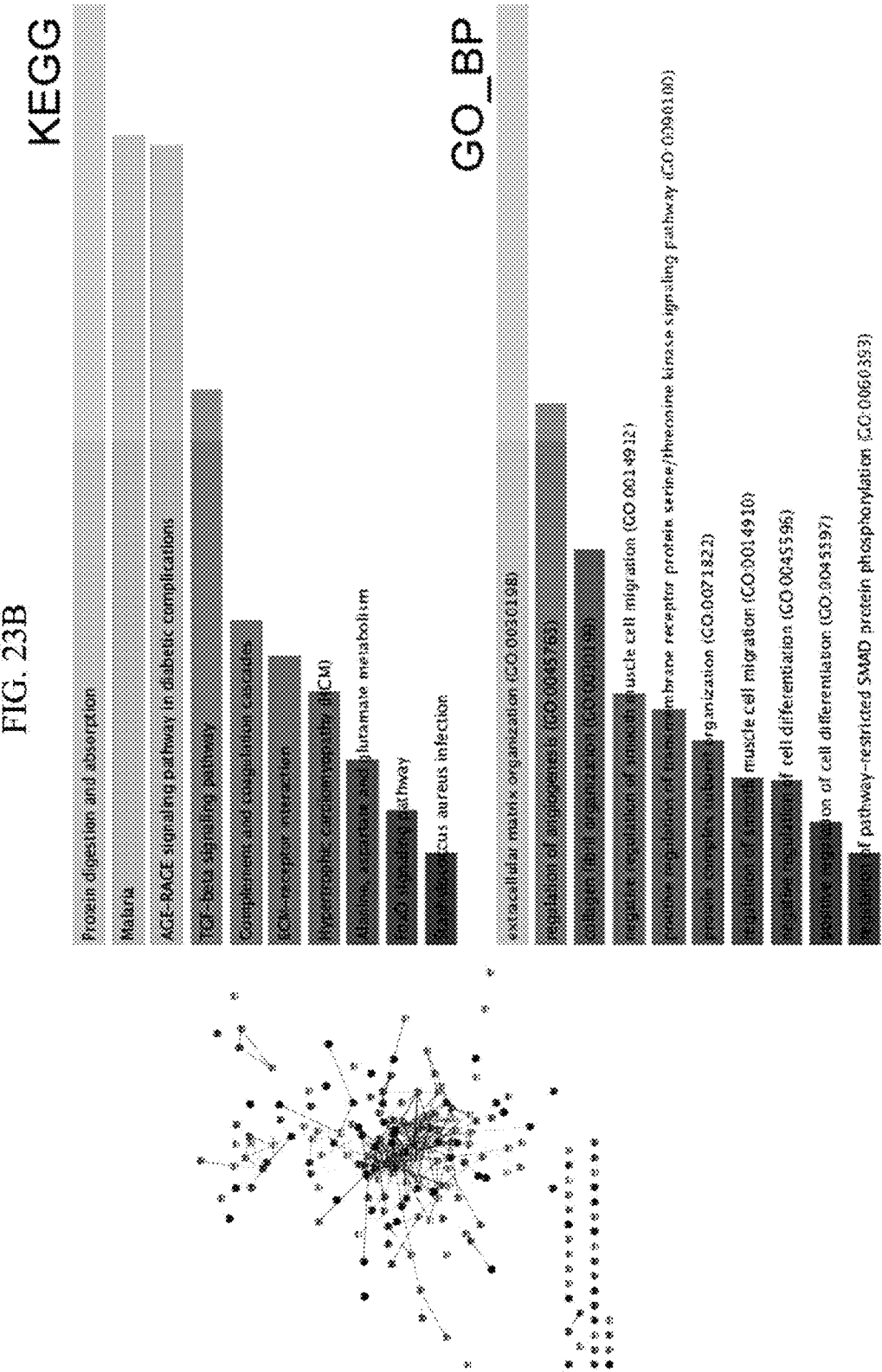
FIG. 23B is of a down-regulated genes with decreased expression, in the cells (HP) that have passed through the microfluidic device of the present invention.

FIG. 23A and FIG. 23B are graphs (right) showing patterns of the genes (HP-UP) with increased expression and the genes (HP-DOWN) with decreased expression in the cells passing through the microfluidic device by the method of the present invention by utilizing the databases of Kyoto Encyclopedia of Genes and Genomes (KEGG) and The Gene Ontology Biological Process (GO_BP) and perspective views showing positions of the genes in the celles by utilizing the GO_BP.

As shown in the two graphs (KEGG and GO_BP based) at right of FIG. 23A, most of the genes showing increased expression in FIG. 22 are genes highly related to a cell cycle or DNA repair, and, as schematically shown at left of FIG. 23A, genes that express proteins mainly present inside cells, in cell membranes, etc. On the contrary, the two graphs at right of FIG. 23B show genes with decreased expression in FIG. 22, which are mainly related to an extracellular matrix (ECM) related to collagen, integrin, and the like. These genes are, as schematically shown at left of FIG. 23B, genes that express proteins mainly located in a matrix outside cells, that is, in the extracellular matrix (ECM), and referring to the existing studies, genes with reduced expression are mainly related to cellular senescence (please refer to Stefanie Sudhop et al., Age related changes in cell stiffness of tendon stem/progenitor cells and a rejuvenating effect of ROCK-inhibition, Biochemical and Biophysical Research Communications 509 2019 839-844; Pinar Zorlutuna et al., Effect of cellular and ECM aging on human iPSC-derived cardiomyocyte performance, maturity and senescence, Biomaterials 268 2021 120554; Toshie Tsuchiya et al., FGF-2 suppresses cellular senescence of human mesenchymal stem cells by down-regulation of TGF-β2, Biochemical and Biophysical Research Communications 359 2007 108-114; Ting-Hein Lee et al., MFG-E8 mediates arterial aging by promoting the proinflammatory phenotype of vascular smooth muscle cells, Journal of Biomedial Science 2019 26:61; Douglas E. Vaughan et al., PAI-1-regulated extracellular proteolysis governs senescence and survival in Klotho mice, PNAS 7090-7095, May 13, 2014, vol. 111, no. 19; Michelle R. Dawson et al., Senescent mesenchymal stem cells remodel extracellular matrix driving breast cancer cells to a more-invasive phenotype, Journal of Cell Science 2020 133, jcs232470. doi:10.1242/jcs.232470; Rui-Ming Liu et al., Serpine 1 induces alveolar type II cell senescence through activating p53-p21-Rb pathway in fibrotic lung disease, Aging Cell 2017 16, pp. 1114-1124; Irit Sagi et al., The ECM path of senescence in aging: components and modifiers, The FEBS Journal 287 2020 2636-2646; Lester F. Lau et al., The Matricellular Protein CCN1/CYR61 Induces Fibroblast Senescence and Restricts Fibrosis in Cutaneous Wound Healing, Nature Cell Biology, Author manuscript, available in PMC 2011 Jan. 1; Marco Demaria et al., Unmasking Transcriptional Heterogeneity in Senescent Cells, Current Biology 27, 2652-2660, Sep. 11, 2017, and the like).

Referring to the aforementioned results, the cellular senescence can be inhibited, delayed, or reversed by applying a physical impact to a cell according to the method of the present invention.

10. Heatmap Analysis of Gene

Figure 24:
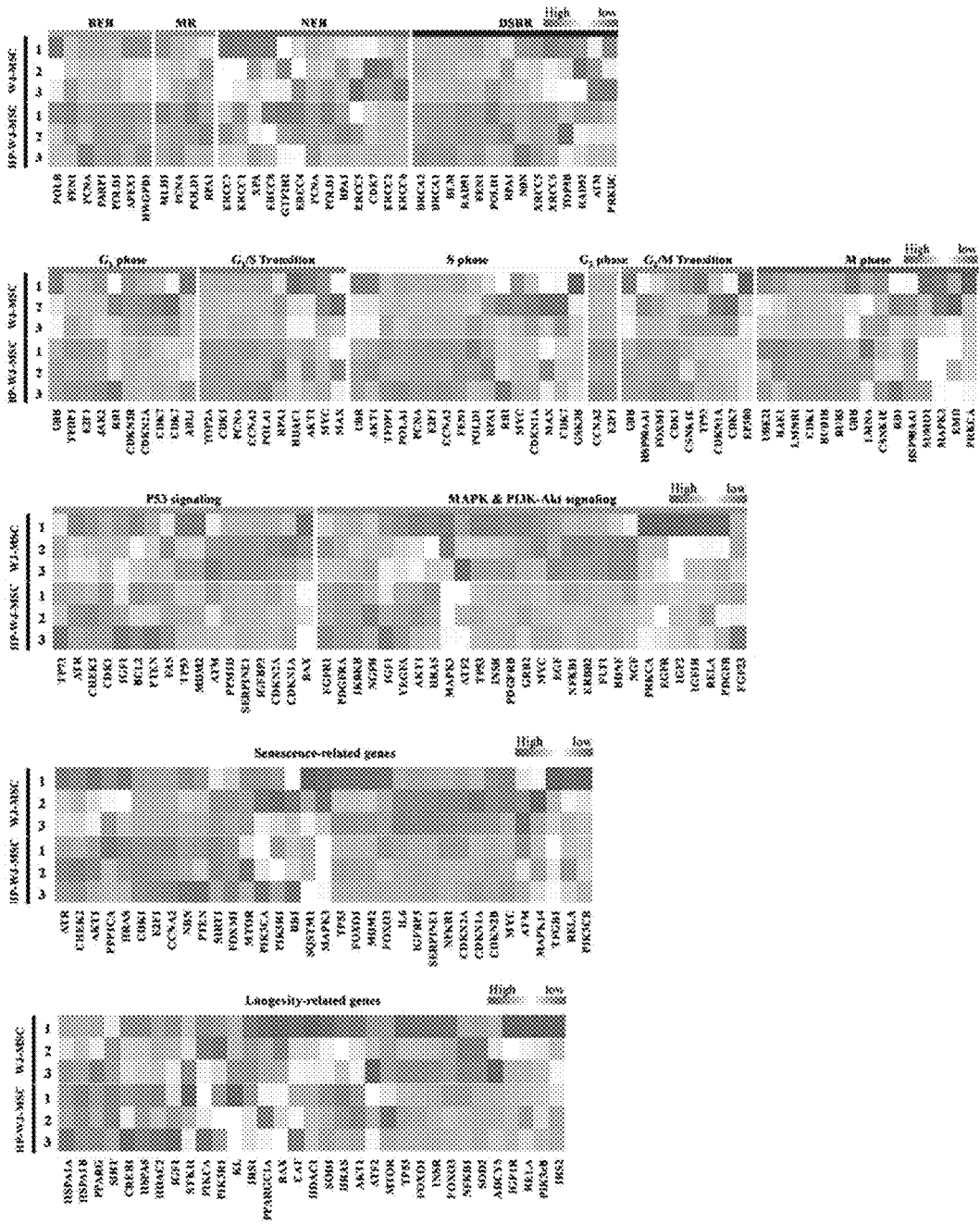
FIG. 24 is a result showing the expression pattern of the genes in the cells (HP) that have passed through the microfluidic device of the present invention through the heatmap analysis compared with the expression level of the gene in the control cell.

As described above, genes with different expressions in the cells subjected to a physical impact through the microfluidic device of the present invention were examined in more detail, by using a Heatmap analysis method, with respect to a DNA repair system, a cell cycle, a p53 mechanism related to cellular senescence, and the like, and the results are shown in FIG. 24.

Referring to FIG. 24, most of genes with increased expression in the cells subjected with a physical impact according to the present invention, although some of the genes exhibited increased expression toward an aging direction, but most of them exhibited increased expression toward a reverse aging (anti-aging) direction, increased or decreased expression toward a cell cycle-activating direction, and decreased expression of aging-inducing genes such as TP53.

As shown in a graph at the top of FIG. 24, BER (base excision repair), MR (mismatch repair), NER (nucleotide excision repair), DSBR (double-strand break repair), etc. are a process of recognizing and correcting DNA damages and then repairing them, which were caused by various stimuli (active oxygen, ultraviolet (UV), X-ray, etc.), and replication errors in the DNA repair system. When this DNA repair process becomes slow or is not well performed, cellular senescence may occur, and phenomena such as tumor formation, apoptosis, and the like may occur. All the genes marked in each corresponding region of FIG. 24 are genes expressing proteins responsible for a role of each region as described above. In addition, a region marked in red a graph of FIG. 24 indicates that expression of the corresponding genes was increased, and a region marked in blue indicates that the expression of the corresponding genes was decreased.

Referring to the results of FIG. 24, most of the genes (PCNA, POLD 1, the like) involved in regulating the above phenomena exhibited increased expressions in the cells passing through the microfluidic device of the present invention. Referring to this result, the cellular senescence was turned out to be inhibited and delayed by the method of the present invention.

11. In vitro Wound Healing Effect

FIG. 13 is photographs showing migration of the cells of umbilical cord-derived mesenchymal stem cells of 7 passages (P7) and 18 passages (P18), and the umbilical cord-derived mesenchymal stem cells of 18 passages treated by the physical impact (Re=244) according to the method of the present invention (P18 HP) over time through a wound healing assay. Specifically, the above cells are filled in the culture dish in a specific density, while maintaining a portion unoccupied. Then, the dishes are cultured in a condition for cell culture for a period of time, and observed for changes in the unoccupied regions. As a result, if the unoccupied regions are filled with the cells due to proliferation, wound healing effects are exhibited. That is, the in vitor wound healing effect is one of functional models of evaluation for migration of cells due to proliferation. Accordingly, if a cell ages, the wound healing effect reduces as the migration or proliferation of cells reduce. Referring to FIG. 13, the cells treated by the physical impact (Re=244) according to the method of the present invention (P18 HP), nevertheless of an aged cell of 18 passages, exhibit similar or superior effects to the cells of the younger 7 passages (P7). On the contrary, the cells of 18 passages (P18), not treated by the physical impact according to the method of the present invention, exhibit reduced effect of wound healing, i.e., reduced migration, during the same period, compared to the other two cells. That is, it is possible to assume that the senescence of a cell may be suppressed, delayed, or reversed by applying a physical impact to the cell in accordance with the method of the present invention.

12. Wound Healing Effect in Animal Model

A wound healing effect of aged mesenchymal stem cells that passed through the microfluidic device (Re=244) of the present invention (P18HP) was confirmed by animal models.

Figure 25:
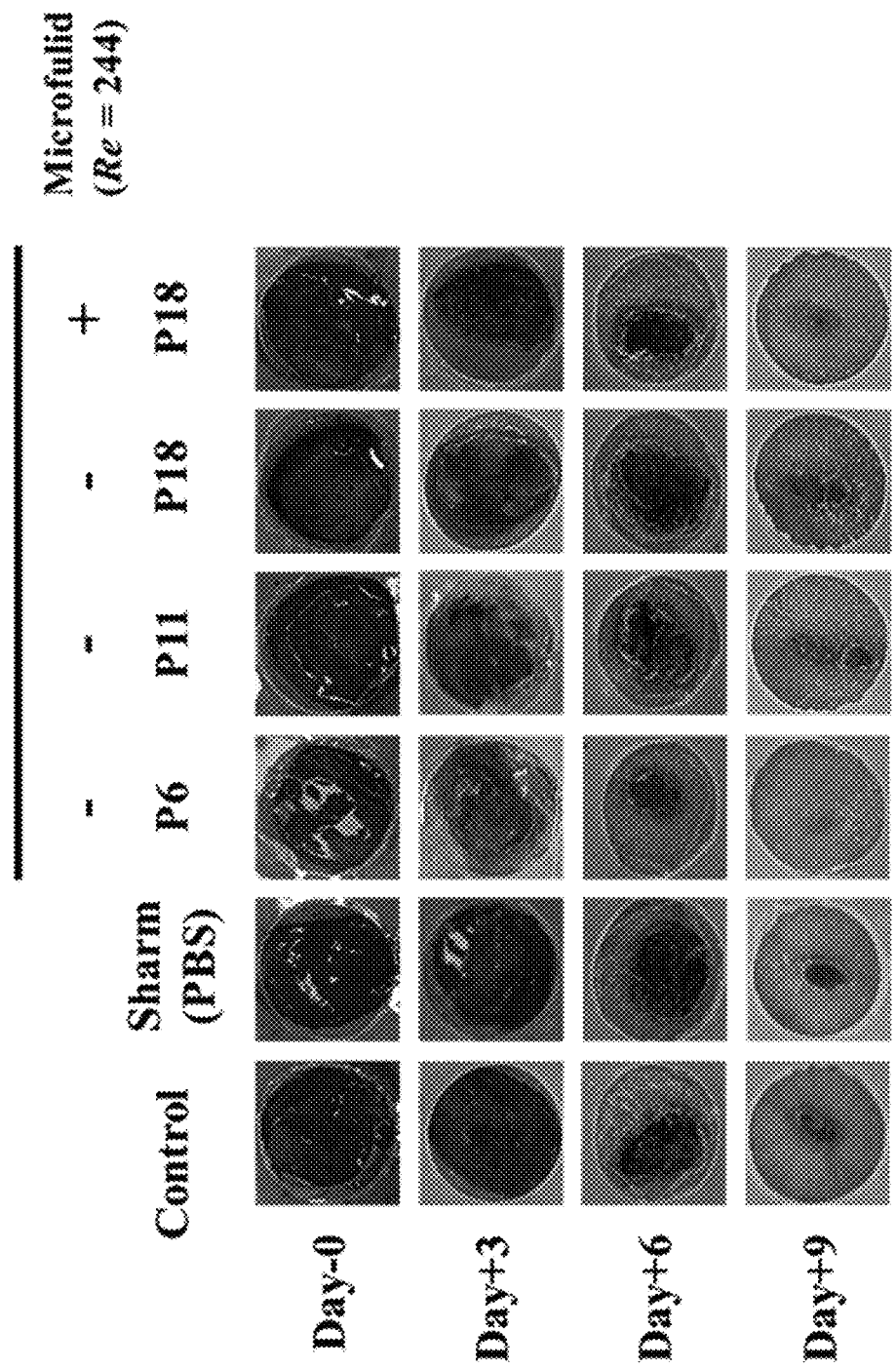
FIG. 25 is a photograph showing the wound healing process over time of the wounded tissues after treating them with each of the stem cells of 6 passages (P6), of 11 passages (P11), of 18 passages (P18), which were not treated by any physical impact according to the invention, the cells that passed through the microfluidic device of the present invention (Re=244) are treated, and only PBS buffer solution that does not include any cell, and the control was not treated at all with any cell or PBS.

FIG. 25 is photographs showing a wound healing process of the groups treated with the mesenchymal stem cells of 6 passages (P6), mesenchymal stem cells of 11 passages (P11), and mesenchymal stem cells of 18 passages (P18), all of which did not pass through the microfluidic device of the invention, and the mesenchymal stem cells of 18 passages that passed through the microfluidic device (Re=244) of the present invention (P18HP), the control group not treated with any cells or PBS, and the group treated with only PBS over time.

Referring to FIG. 25, the aged mesenchymal stem cells (P18HP) passing through microfluidic device (Re=244) of the present invention exhibited similar wound healing activity to that of young stem cells (the stem cells of 6 passages, that is, P6). The cells passing through the microfluidic device of the present invention, which were aged mesenchymal stem cells of 18 passages subjected to a physical impact through the microfluidic device of the present invention, exhibited more excellent wound healing effect than young mesenchymal stem cells of 11 passages. On the other hand, the mesenchymal stem cells of 18 passages (P18) subjected with a physical impact through the microfluidic device of the present invention still showed a wide wound site even on the $9^{th}$ day after the wounding and greatly low wound healing activity, compared with the cells subjected with a physical impact according to the present invention.

Figure 26:
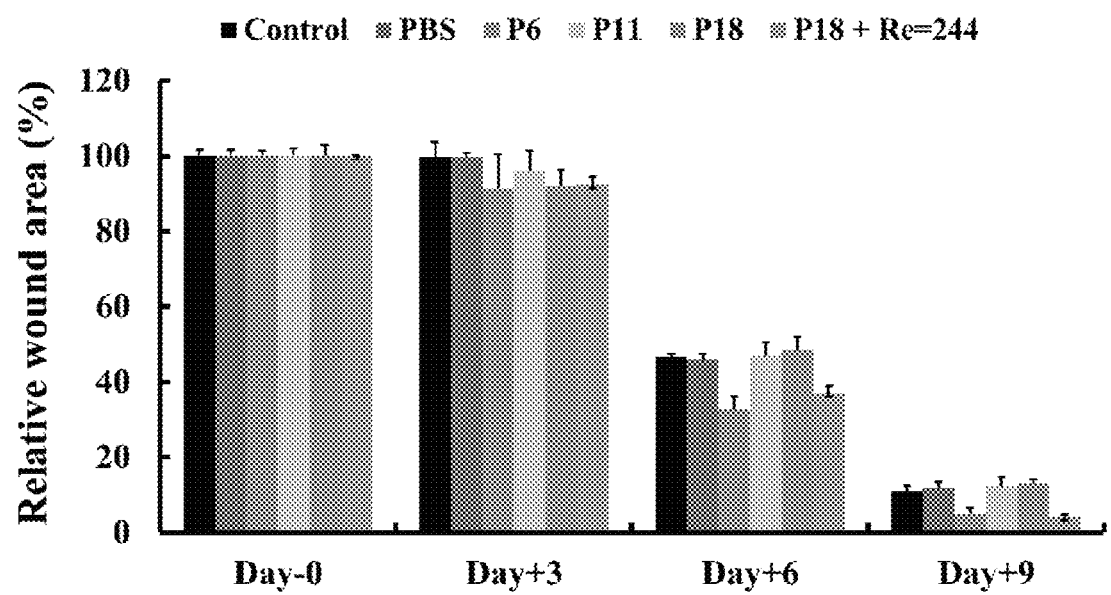
FIG. 26 is a graph showing the relative wound area over time of the wound healing models of FIG. 25.

FIG. 26 is a graph showing relative wound areas of the tissues of FIG. over time. Referring to FIG. 26, the wound area of the tissues treated with the cells passing through the microfluidic device according to the present invention was similar to those treated with the cells of P6 or P18 on the $3^{rd}$ day from the wounding, and accordingly, in all these tissues, the wound areas did not almost decrease. However, the wound areas of all the tissues were greatly reduced from the $6^{th}$ day after the wounding, and among them, the tissue treated with the cells passing through the microfluidic device of the present invention, when compared with the control group, or the groups treated with P11, or P18 cells, exhibited a little larger wound area than that treated with P6, but 25% or more smaller wound areas than the other groups, and thus excellent wound healing activity. In addition, on the 9$^{th}$ day from the wounding, all the tissues exhibited greatly decreased wound areas, but among them, the tissue treated with the cells passing through the microfluidic device of the present invention along with the tissue treated with the P6 cells exhibited greatly reduced wound areas down to greater than or equal to about ⅓ of those of the other tissues. In other words, the cells subjected with a physical impact through the microfluidic device of the present invention, even though very aged cells of 18 passages, were reversely aged and turned out to have similarly excellent wound healing activity to that of young cells of 6 passages. In other words, the cells passing through the microfluidic device of the present invention turned out to be reversely aged.

Figure 27:
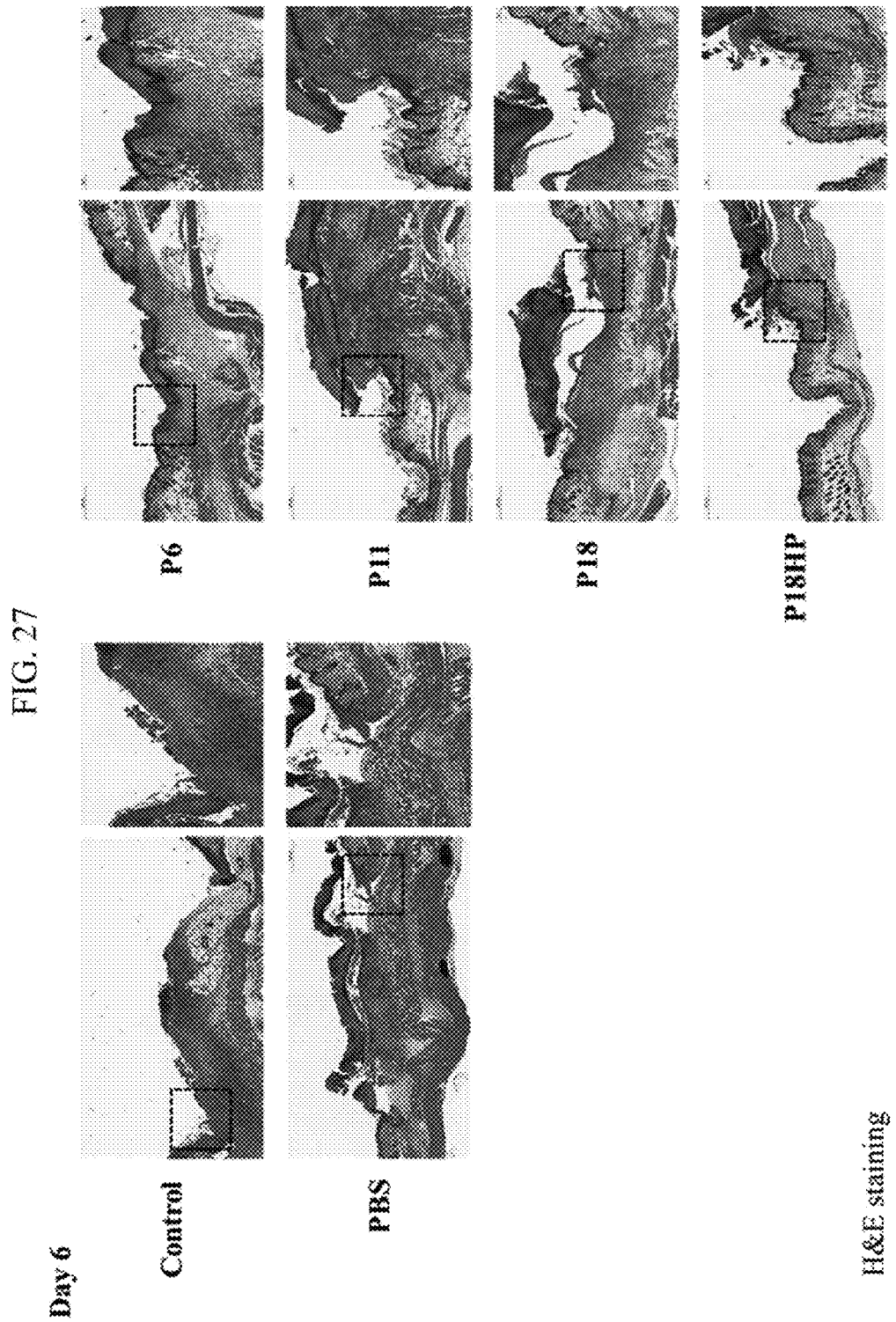
FIG. 27 is H&E staining photographs of the wound healing models of FIG. 25 for confirming tissue necrosis on the 6th day after the wounding.

As shown from FIG. 26, since wound healing activity of all cells was activated from the 6$^{th}$ day of the wounding, H&E staining was performed to check whether or not intracellular tissues were necrotic due to inflammation of each cell, and the results are shown in FIG. 27. As shown from FIG. 27, on the 6$^{th}$ day of the wounding, the tissue necrosis treated with the young cells of P6 and the cells according to the present invention was relatively very lower than that of the other cells.

Figure 28:
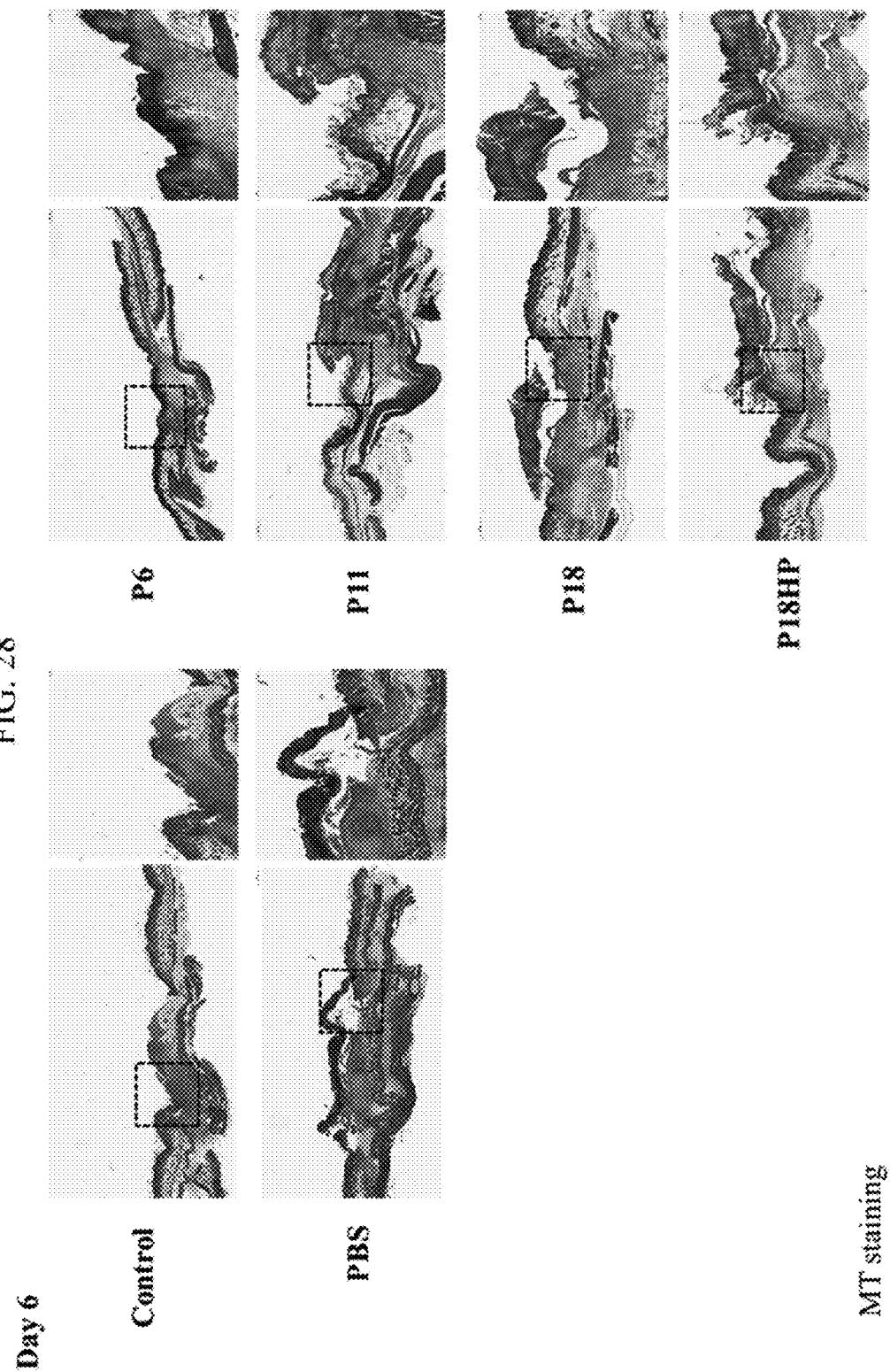
FIG. 28 is a MT (Masson-Trichome) staining photograph of the wound healing models of FIG. 25 for confirming the tissue-to-tissue binding ability on the 6th day after the wounding.

Additionally, MT (Masson-Trichome) staining was performed in order to check tissue-to-tissue binding ability of the tissues with collagen and the like on the 6$^{th}$ day of the wounding, and the results are shown in FIG. 28. As shown from FIG. 28, the tissues treated with the cells according to the present invention and P6 cells had a narrow gap between the tissues and collagen, which shows excellent binding ability. On the contrary, the tissues treated with P11 and P18 cells exhibit a wide gap between the tissues and collagen, and particularly, the tissue treated with P18 cells had a very wider gap. In contrast, the tissues treated with the cells treated by a physical impact through the microfluidic device according to the present invention exhibits not so narrow a gap as that of P6 but had a much narrower gap between the tissues and collagen than P11, and accordingly, exhibited improved binding ability.

Through the above experiments, by applying a physical impact through the microfluidic device according to the present invention, it is possible to inhibit, delay, or reverse the cellular senescence. As such, the cells whose senescence is inhibited, delayed, or reversed, may maintain the same or similar activity as or to the younger cells.

As described above in detail a specific part of the present invention, for those of ordinary skill in the art, this specific description is only a desirable embodiment, and it is clear that the scope of the present invention is not limited thereto. Accordingly, the substantial scope of the present invention will be defined by the appended claims and their equivalents.

What is claimed is:

1. A method for inhibiting, delaying, or reversing cellular senescence, comprising:

having an isolated cell flow; and crashing the cell into an impact surface installed on a flow path of the cell to apply a physical impact to the cell, whereby a reorganization of cytoskeleton occurs in the cell without causing cell death, wherein the having an isolated cell flow is performed by injecting a fluid containing the cell into a microchannel to flow in accordance with a predetermined parameter (Re), wherein the parameter (Re) is determined by Equation 1:

$$Re = \rho VD/\mu \qquad \text{(Equation 1)}$$

wherein, in Equation 1, $\rho$ is a density of the fluid, V is a velocity of the fluid, D is a characteristic length of the fluid, and $\mu$ is a viscosity coefficient of the fluid, and wherein the parameter (Re) has a value of from 75 to 290.

2. The method of claim 1, wherein the having a cell flow is performed under a condition that the parameter (Re) has a value of from about 81 to about 285.

3. The method of claim 1, wherein the having a cell flow is performed under a condition that the parameter (Re) has a value of from about 100 to about 280.

4. The method of claim 1, wherein a distance from a point where the cell start to flow in the microchannel to the impact surface is from about 0.1 mm to about 50 mm.

5. The method of claim 1, wherein a distance from a point where the cell start to flow in the microchannel to the impact surface is from about 5 mm to about 30 mm.

6. The method of claim 1, wherein an angle between an axis of the flow path and the impact surface is from about 10 degrees to about 170 degrees.

7. The method of claim 1, wherein an angle between an axis of the flow path and the impact surface is from about 20 degrees to about 160 degrees.

8. The method of claim 1, wherein the cell comprises a cell derived from a living body comprising a fibroblast; a stem cell comprising a mesenchymal stem cell, an embryonic stem cell, an induced pluripotent stem cell, or a combination thereof; an immune cell comprising a T cell, an NK cell, a B cell, a dendritic cell, a macrophage, or a combination thereof; a precursor cell of the cell derived from a living body, a stem cell, or an immune cell; or a combination of the above cells.

9. The method of claim 8, wherein the fibroblast comprises a skin-derived fibroblast, and the stem cell comprises a mesenchymal stem cell.

10. The method of claim 9, wherein the mesenchymal stem cell is an umbilical cord-derived mesenchymal stem cell (WJ-MSC).

\* \* \* \* \*